United States Patent [19]

Hughes, Jr. et al.

[11] Patent Number: 5,939,301
[45] Date of Patent: Aug. 17, 1999

[54] **CLONED DNA POLYMERASES FROM *THERMOTOGA NEAPOLITANA* AND MUTANTS THEREOF**

[75] Inventors: A. John Hughes, Jr., Germantown; Deb K. Chatterjee, N. Potomac, both of Md.

[73] Assignee: Life Technologies, Inc., Rockville, Md.

[21] Appl. No.: 08/537,400

[22] Filed: Oct. 2, 1995

Related U.S. Application Data

[63] Continuation-in-part of application No. 08/370,190, Jan. 9, 1995, which is a continuation-in-part of application No. 08/316,423, Sep. 30, 1994, abandoned.

[51] Int. Cl.⁶ ............................. C12N 9/12; C12N 15/54
[52] U.S. Cl. ................ 435/194; 435/252.3; 435/252.33; 435/325; 435/419; 536/23.2
[58] Field of Search ............................... 435/194, 252.3, 435/252.33, 325, 419; 536/23.2

[56] References Cited

U.S. PATENT DOCUMENTS

| | | | |
|---|---|---|---|
| H1531 | 5/1996 | Blumentals et al. | 435/194 |
| 4,795,699 | 1/1989 | Tabor et al. | 435/5 |
| 4,889,818 | 12/1989 | Gelfand et al. | 435/194 |
| 5,047,342 | 9/1991 | Chatterjee | 435/194 |
| 5,614,365 | 3/1997 | Tabor et al. | 435/194 |
| 5,624,833 | 4/1997 | Gelfand et al. | 435/194 |

FOREIGN PATENT DOCUMENTS

| | | |
|---|---|---|
| WO 92/03556 | 3/1992 | WIPO . |
| WO 92/06200 | 4/1992 | WIPO . |
| WO 92/06202 | 4/1992 | WIPO . |
| 0 655 506 | 5/1995 | WIPO . |
| WO96/38568 | 12/1996 | WIPO . |

OTHER PUBLICATIONS

Derbyshire et al., The 3'-5' exonuclease of DNA polymerase I of *Escherichial coli:* contribution of each amino acid at the active site to the reaction, EMBO J. 10: 17–24 (1990).

Derbyshire et al., Genetic and Crystallographic Studies of the 3',5'-Exonucleolytic Site of DNA Polymerase I, *Science*, vol. 240, 199–201 (1988).

Polesky et al., Side Chains Involved in Catalysis of the Polymerase Reaction of DNA Polymerase I from *Escherichia coli, The Journal of Biological Chemistry*, vol. 267, No. 12: 8417–8428 (1992).

Antonio Bernad et al., A Conserved 3'–5' Exonuclease Active Site in Prokaryotic and Eukaryotic DNA Polymerases, *Cell*, vol. 59: 219–228 (1989).

Slater et al., "DNA Polymerase I of Thermatoga Neopolitane (Tne) and Mutant Derivatives," Seventh International Genome Sequencing and Analysis Conference, Sep. 16–20, 1995, Abstract.

Shengyu et al., Heat–Stable DNA Polymerase I Large Fragment Resolves Hairpin Structure In DNA Sequencing, Scientia Sinica (Series B), vol. XXX; 503–507 (1987).

Astatke, M., et al., "Deoxynucleoside Triphosphate and Pyrophosphate Binding Sites in the Catalytically Competent Ternary Complex for the Polymerase Reaction Catalyzed by DNA Polymerase I (Klenow Fragment)," *J. Biol. Chem.* 270(4):1945–1954 (Jan. 27, 1995).

Bergquist, P.L., et al., "Genetics and Potential Biotechnological Applications of Thermophilic and Extremely Thermophilic Microorganisms," *Biotech. Genet. Eng. Rev.* 5:199–244 (1987).

Blanco, L., et al., "Evidence Favouring the Hypothesis of a Conserved 3'–5' Exonuclease Active Site in DNA–dependent DNA Polymerases," *Gene 112:*139–144 (1992).

Braithwaite, D.K., and Ito, J., "Compilation, Alignment, and Phylogenetic Relationships of DNA Polymerases," *Nucl. Acids Res.* 21(4):787–802 (Feb. 25, 1993).

Chien, A., et al., "Deoxyribonucleic Acid Polymerase from the Extreme Thermophile *Thermus aquaticus,"* J. Bacteriol. 127(3):1550–1557 (1976).

Darzins, A., and Chakrabarty, A.M., "Cloning of Genes Controlling Alginate Biosynthesis from a Mucoid Cystic Fibrosis Isolate of *Pseudomonas aeruginosa,"* J. Bacteriol. 159(1):9–18 (1984).

Elie, C., et al., "Thermostable DNA Polymerase from the Archaebacterium *Sulfolobus acidocaldarius.* Purification, Characterization and Immunological Properties," *Eur. J. Biochem.* 178:619–626 (1989).

Freemont, P.S., et al., "A Domain of the Klenow Fragment of *Escherichia coli* DNA Polymerase I Has Polymerase but No Exonuclease Activity," *Proteins 1(1):*66–73 (1986).

Gerard, G.F., et al., "Poly(2'–O–methyl cytidylate)•Oligodeoxyguanylate as a Template for the Ribonucleic Acid Directed Deoxyribonucleic Acid Polymerase in Ribonucleic Acid Tumor Virus Particles and a Specific Probe for the Ribonucleic Acid Directed Enzyme in Transformed Murine Cells," *Biochemistry 13(8)*:1632–1641 (1974).

(List continued on next page.)

*Primary Examiner*—Keith D. Hendricks
*Attorney, Agent, or Firm*—Sterne, Kessler, Goldstein & Fox P.L.L.C.

[57] ABSTRACT

The invention relates to a substantially pure thermostable DNA polymerase from *Thermotoga neapolitana* (Tne) and mutants thereof. The Tne DNA polymerase has a molecular weight of about 100 kilodaltons and is more thermostable than Taq DNA polymerase. The mutant Tne DNA polymerase has at least one mutation selected from the group consisting of (1) a first mutation that substantially reduces or eliminates 3'→5' exonuclease activity of said DNA polymerase; (2) a second mutation that substantially reduces or eliminates 5'→3' exonuclease activity of said DNA polymerase; (3) a third mutation in the O helix of said DNA polymerase resulting in said DNA polymerase becoming non-discriminating against dideoxynucleotides. The present invention also relates to the cloning and expression of the wild type or mutant Tne DNA polymerase in *E. coli*, to DNA molecules containing the cloned gene, and to host cells which express said genes. The Tne DNA polymerase of the invention may be used in well-known DNA sequencing and amplification reactions.

38 Claims, 10 Drawing Sheets

OTHER PUBLICATIONS

Gutman, P.D., and Minton, K.W., "Conserved Sites in the 5'–3' Exonuclease Domain of *Escherichia coli* DNA Polymerase," *Nucl. Acids Res.* 21(18):4406–4407 (Sep. 11, 1993).

Huber, R., et al., "*Thermotoga maritima* sp. nov. Represents a New Genus of Unique Extremely Thermophilic Eubacteria Growing Up to 90°C.," *Arch. Microbiol.* 144:324–333 (1986).

Huser, B.A., et al., "Isolation and Characterisation of a Novel Extremely Thermophilic, Anaerobic, Chemo–Organotrophic Eubacterium," *FEMS Microbiol. Letts.* 37:121–127 (1986).

Jannasch, H.W., et al., "*Thermotoga neapolitana* sp. nov. of the Extremely Thermophilic, Eubacterial Genus Thermotoga," *Arch. Microbiol.* 150(1):103–104 (May 1988).

Joyce, C.M., et al., "Nucleotide Sequence of the *Escherichia coli* polA Gene and Primary Structure of DNA Polymerase I," *J. Biol. Chem.* 257(4):1958–1964 (1982).

Joyce, C.M., "Can DNA Polymerase I (Klenow Fragment) Serve as a Model for Other Polymerases?," *Curr. Opin. Struct. Biol.* 1(1):123–129 (1991).

Joyce, C.M., and Steitz, T.A., "Function and Structure Relationships in DNA Polymerases," *Annu. Rev. Biochem.* 63:777–822 (Jul. 1994).

Kaboev, O.K., et al., "Purification and Properties of Deoxyribonucleic Acid Polymerase from *Bacillus stearothermophilus*," *J. Bacteriol.* 145(1):21–26 (1981).

Kaledin, A.S., et al., "Isolation and Properties of DNA Polymerase from Extremely Thermophilic Bacterium *Thermus aquaticus* YT1," *Biokhimiya* 45(4):644–651 (1980).

Kelly, R.M., and Deming, J.W., "Extremely Thermophilic Archaebacteria: Biological and Engineering Considerations," *Biotechnol. Prog.* 4(2):47–62 (1988).

Klimczak, L.J., et al., "Purification and Characterization of DNA Polymerase from the Archaebacterium *Methanobcaterium thermoautotrophicum*," *Biochemistry* 25:4850–4855 (1986).

Lin, T.–C., et al., "Cloning and Expression of T4 DNA Polymerase," *Proc. Natl. Acad. Sci. USA* 84:7000–7004 (1987).

Minkley, E.G., et al., "*Escherichia coli* DNA Polymerase I. Construction of a polA Plasmid for Amplification and an Improved Purification Scheme," *J. Biol. Chem.* 259(16):10386–10392 (1984).

Modak, M.J., and Marcus, S.L., "Purification and Properties of Rauscher Leukemia Virus DNA Polymerase and Selective Inhibition of Mammalian Viral Reverse Transcriptase by Inorganic Phosphate," *J. Biol. Chem.* 252(1):11–19 (1977).

Ollis, D.L., et al., "Structure of Large Fragment of *Escherichia coli* DNA Polymerase I Complexed with dTMP," *Nature* 313:762–766 (1985).

Polesky, A.H., et al., "Identification of Residues Critical for the Polymerase Activity of the Klenow Fragment of DNA Polymerase I from *Escherichia coli*," *J. Biol. Chem.* 265(24):14579–14591 (1990).

Rossi, M., et al., "Structure and Properties of a Thermophilic and Thermostable Polymerase Isolated from *Sulfolobus solfataricus*," *System. Appl. Microbiol.* 7:337–341 (1986).

Sagner, G., et al., "Rapid Filter Assay for the Detection of DNA Polymerase Activity: Direct Identification of the Gene for the DNA Polymerase from *Thermus aquaticus*," *Gene* 97:119–123 (1991).

Simpson, H.D., et al., "Purification and Some Properties of a Thermostable DNA Polymerase from a Thermotoga Species," *Biochem. Cell Biol.* 68:1292–1296 (1990).

Spadari, S., and Weissbach, A., "HeLa Cell R–Deoxyribonucleic Acid Polymerases. Separation and Characterization of Two Enzymatic Activities," *J. Biol. Chem.* 249(18):5809–5815 (1974).

Stenesh, J., and Roe, B.A., "DNA Polymerase from Mesophilic and Thermophilic Bacteria. I. Purification and Properties of DNA Polymerase from *Bacillus licheniformis* and *Bacillus stearothermophilus*," *Biochim. Biophys. Acta* 272:156–166 (1972).

Tabor, S., and Richardson, C.C., "A Single Residue in DNA Polymerases of the *Escherichia coli* DNA Polymerase I Family is Critical for Distinguishing Between Deoxy– and Dideoxyribonucleotides," *Proc. Natl. Acad. Sci. USA* 92:6339–6343 (Jul. 1995).

Windberger, E., et al., "*Thermotoga thermarum* sp. nov. and *Thermotoga neapolitana* Occurring in African Continental Solfataric Springs," *Arch. Microbiol.* 151(6):506–512 (May 1989).

A copy of the International Search Report for the corresponding PCT Application, International Application No. PCT/US95/12358.

```
      Bam HI
  1   GGATCCAGAC TGGTGGATCG TCAGTGCGGA TTATTCCCAA ATAGAACTCA GAATCCTCGC
        G  S  R   L  V  D    R  Q  C  G   L  F  P  N    R  T  Q  N    P  R
   →    D  P  D   W  W  I    V  S  A  D   Y  S  Q  I    E  L  R  I    L
             I  Q  T   G  G  S    S  V  R  I    I  P  K   -  N  S    E  S  S

61   TCATCTCAGT GGTGATGAGA ACCTTGTGAA GGCCTTCGAG GAGGGCATCG ATGTGCACAC
        S  S  Q   W  -  -    E  P  C  E   G  L  R    G  G  H   R  C  A  H
   →  A  H  L  S   G  D  E    N  L  V    K  A  F  E    E  G  I    D  V  H
           L  I  S  V    V  M  R  T    L  -  R  P    S  R  R    A  S  M  C  T

121   CTTGACTGCC TCCAGGATCT ACAACGTAAA GCCAGAAGAA GTGAACGAAG AAATGCGACG
        L  D  C   L  Q  D    L  Q  R  K   A  R  R    S  E  R    R  N  A  T
   →  T  L  T  A   S  R  I    Y  N  V    K  P  E  E    V  N  E    E  M  R
           P  -  L  P    P  G  S  T    T  -  S  Q    K  K  -    T  K  K  C  D

181   GGTTGGAAAG ATGGTGAACT TCTCTATAAT ATACGGTGTC ACACCGTACG GTCTTTCTGT
        G  W  K   D  G  E    L  L  Y  N   I  R  C    H  T  V    R  S  F  C
   →  R  V  G  K   M  V  N  Ⓕ  S  I  I    Y  G  V    T  P  Y  G  L  S
           G  L  E  R    W  -  T    S  L  -  Y    T  V  S    H  R  T    V  F  L

241   GAGACTTGGA ATACCGGTTA AGAAGCAGA AAAGATGATT ATCAGCTATT CACACTGTA
        E  T  W   N  T  G    -  R  S  R   K  D  D    Y  Q  L    F  H  T  V
   →  V  R  L  G   I  P  V    K  E  A  E    K  M  I    I  S  Y    F  T  L
           -  D  L  E    Y  R  L    K  K  Q  K  R    -  L  S    A  I  S  H  C

301   TCCAAAGGTG CGAAGCTACA TCCAGCAGGT TGTTGCAGAG GCAAAAGAGA AGGGCTACGT
        S  K  G   A  K  L    H  P  A  G   C  C  R    G  K  R    E  G  L  R
   →  Y  P  K  V   R  S  Y  I    Q  Q  V    V  A  E    A  K  E  K    G  Y
          I  Q  R  C    E  A  T  S    S  R  L    L  Q  R    Q  K  R  R    A  T

361   CAGGACTCTC TTTGGAAGAA AAAGAGATAT TCCCCAGCTC ATGGCAAGGG ACAAGAACAC
        Q  D  S   L  W  K    K  K  R  Y   S  P  A    H  G  K    G  Q  E  H
   →  V  R  T  L   F  G  R    K  R  D  I    P  Q  L    M  A  R    D  K  N
           S  G  L  S    L  E  E    K  E  I  F    P  S  S    W  Q  G    T  R  T

421   CCAGTCCGAA GGCGAAAGAA TCGCAATAAA CACCCCCATT CAGGGAACTG CGGCAGATAT
        P  V  R   R  R  K    N  R  N  K   H  P  H    S  G  N    C  G  R  Y
   →  T  Q  S  E   G  E  R    I  A  I  N    T  P  I    Q  G  T    A  A  D
          P  S  P  K    A  K  E    S  Q  -  T    P  P  F    R  E  L    R  Q  I

481   AATAAAATTG CTATGATAG ATATAGACGA GGAGCTGAGA AAAAGAAACA TGAAATCCAG
        N  K  I   G  Y  D    R  Y  R  R   G  A  E    K  K  K    H  E  I  Q
   →  I  I  K  L   A  M  I    D  I  D  E    E  L  R    K  R  N    M  K  S
            -  -  N  W    L  -  -    I  -  T  R    S  -  E    K  E  T    -  N  P
```

FIG. 5A

```
541    AATGATCATT CAGGTTCATG ACGAACTGGT CTTCGAGGTT CCCGATGAGG AAAAAGAAGA
         N D H   S G S   - R T G   L R G   S R -   G K R R
    →  R M I I   Q V H   D E L V   F E V   P D E   E K E
         E -   S F   R F M   T N W S   S R F   P M R   K K K

601    ACTAGTTGAT CTGGTGAAGA ACAAAATGAC AAATGTGGTG AAACTCTCTG TGCCTCTTGA
         T S -   S G E   E Q N D   K C G   E T L   C A S -
    →  E L V D   L V K   N K M T   N V V   K L S   V P L
         N -   L I   W -   R T K   - Q M W   -   N S L   C L L

661    GGTTGACATA AGCATCGGAA AAAGCTGGTC TTGA
         G -   H K H R   K K L V   L
    →  E V D I   S I G   K S W S   -
         R L T   -   A S E   K A G L
```

FIG. 5B

CLONED DNA POLYMERASES FROM *THERMOTOGA NEAPOLITANA* AND MUTANTS THEREOF

CROSS-REFERENCE TO RELATED APPLICATIONS

This application is a continuation-in-part of U.S. application Ser. No. 08/370,190, filed Jan. 9, 1995, entitled "Cloned DNA Polymerases from *Thermotoga neapolitana*," which is a continuation-in-part of U.S. application Ser. No. 08/316,423, filed Sep. 30, 1994, entitled "Cloned DNA Polymerases from *Thermotoga neapolitana*," now abandoned. The contents of each of these applications are incorporated herein by reference.

BACKGROUND OF THE INVENTION

1. Field of the Invention

The present invention relates to a substantially pure thermostable DNA polymerase. Specifically, the DNA polymerase of the present invention is a *Thermotoga neapolitana* DNA polymerase having a molecular weight of about 100 kilodaltons. The present invention also relates to the cloning and expression of the *Thermotoga neapolitana* DNA polymerase in *E. coli*, to DNA molecules containing the cloned gene, and to hosts which express said genes. The DNA polymerase of the present invention may be used in DNA sequencing and amplification reactions.

This invention also relates to mutants of the *Thermotoga neapolitana* (Tne) DNA polymerase, having substantially reduced 3'→5' exonuclease activity; mutants of *Thermotoga neapolitana* containing a Phe$^{67}$→Tyr$^{67}$ (as numbered in FIG. 5) mutation resulting in the ability of the mutant DNA polymerase to incorporate dideoxynucleotides into a DNA molecule about as efficiently as deoxynucleotides; and mutants having substantially reduced 5'→3' exonuclease activity. The Tne mutants of this invention can have one or more of these properties. These Tne DNA polymerase mutants may also be used in DNA sequencing and amplification reactions.

2. Background Information

DNA polymerases synthesize the formation of DNA molecules which are complementary to a DNA template. Upon hybridization of a primer to the single-stranded DNA template, polymerases synthesize DNA in the 5' to 3' direction, successively adding nucleotides to the 3'-hydroxyl group of the growing strand. Thus, in the presence of deoxyribonucleoside triphosphates (dNTPs) and a primer, a new DNA molecule, complementary to the single stranded DNA template, can be synthesized.

A number of DNA polymerases have been isolated from mesophilic microorganisms such as *E coli*. A number of these mesophilic DNA polymerases have also been cloned. Lin et al. cloned and expressed T4 DNA polymerase in *E. coil* (*Proc. Natl. Acad. Sci. USA* 84:7000–7004 (1987)). Tabor et al. (U.S. Pat. No. 4,795,699) describes a cloned T7 DNA polymerase, while Minkley et al. (*J. Biol. Chem.* 259:10386–10392 (1984)) and Chatterjee (U.S. Pat. No. 5,047,342) described *E. coli* DNA polymerase I and the cloning of T5 DNA polymerase, respectively.

Although DNA polymerases from thermophiles are known, relatively little investigation has been done to isolate and even clone these enzymes. Chien et al., *J. Bacteriol.* 127:1550–1557 (1976) describe a purification scheme for obtaining a polymerase from *Thermus aquaticus* (Taq). The resulting protein had a molecular weight of about 63,000 daltons by gel filtration analysis and 68,000 daltons by sucrose gradient centrifugation. Kaledin et al., *Biokhymiya* 45:644–51 (1980) disclosed a purification procedure for isolating DNA polymerase from *T. aquaticus* YT1 strain. The purified enzyme was reported to be a 62,000 dalton monomeric protein. Gelfand et al. (U.S. Pat. No. 4,889,818) cloned a gene encoding a thermostable DNA polymerase from *Thermus aquaticus*. The molecular weight of this protein was found to be about 86,000 to 90,000 daltons.

Simpson et al. purified and partially characterized a thermostable DNA polymerase from a Thermotoga species (*Biochem. Cell. Biol.* 86:1292–1296 (1990)). The purified DNA polymerase isolated by Simpson et al. exhibited a molecular weight of 85,000 daltons as determined by SDS-polyacrylamide gel electrophoresis and size-exclusion chromatography. The enzyme exhibited half-lives of 3 minutes at 95° C. and 60 minutes at 50° C. in the absence of substrate and its pH optimum was in the range of pH 7.5 to 8.0. Triton X-100 appeared to enhance the thermostability of this enzyme. The strain used to obtain the thermostable DNA polymerase described by Simpson et al. was Thermotoga species strain FjSS3-B. 1 (Hussar et al., *FEMS Microbiology Letters* 37:121–127 (1986)). Other DNA polymerases have been isolated from thermophilic bacteria including *Bacillus steraothermophilus* (Stenesh et al., *Biochim. Biophys. Acta* 272:156–166 (1972); and Kaboev et al., *J. Bacteriol.* 145:21–26 (1981)) and several archaebacterial species (Rossi et al., *System. Appl. Microbiol.* 7:337–341 (1986); Klimczak et al., Biochemistry 25:4850–4855 (1986); and Elie et al., *Eur. J. Biochem.* 178:619–626 (1989)). The most extensively purified archaebacterial DNA polymerase had a reported half-life of 15 minutes at 87° C. (Elie et al. (1989), supra). Innis et al., In PCR *Protocol: A Guide To Methods and Amplification*, Academic Press, Inc., San Diego (1990) noted that there are several extreme thermophilic eubacteria and archaebacteria that are capable of growth at very high temperatures (Bergquist et al., *Biotech. Genet. Eng. Rev.* 5:199–244 (1987); and Kelly et al., *Biotechnol Prog.* 4:47–62 (1988)) and suggested that these organisms may contain very thermostable DNA polymerases.

In many of the known polymerases, the 5'→3' exonuclease activity is present in the N-terminal region of the polymerase. (Ollis, et al., *Nature* 313:762–766 (1985); Freemont et al., *Proteins* 1:66–73 (1986); Joyce, *Cur. Opin. Struct. Biol.* 1:123–129 (1991).) There are some conserved amino acids that are thought to be responsible for the 5'→3' exonuclease activity. (Gutman & Olinton, *Nucl. Acids Res.* 21:4406–4407 (1993).) These amino acids include Tyr$^{22}$, Gly$^{103}$, Gly$^{187}$, and Gly$^{192}$ in *E. coli* polymerase I. Any mutation of these amino acids would reduce 5'-to-3' exonuclease activity. It is known that the 5'-exonuclease domain is dispensable. The best known example is the Klenow fragment of *E. coli* polymerase I. The Klenow fragment is a natural proteolytic fragment devoid of 5'-exonuclease activity (Joyce et. al., *J. Biol. Chem.* 257:1958–64 (1990).) Polymerases lacking this activity are useful for DNA sequencing.

Most DNA polymerases also contain a 3'→5' exonuclease activity. This exonuclease activity provides a proofreading ability to the DNA polymerase. A T5 DNA polymerase that lacks 3'→5' exonuclease activity is disclosed in U.S. Pat. No. 5,270,179. Polymerases lacking this activity are useful for DNA sequencing.

The polymerase active site, including the dNTP binding domain is usually present at the carboxyl terminal region of the polymerase (Ollis et al., *Nature* 313:762–766 (1985); Freemont et al., *Proteins* 1:66–73 (1986)). It has been shown that Phe$^{762}$ of *E. coli* polymerase I is one of the amino acids that directly interacts with the nucleotides (Joyce & Steitz, *Ann. Rev. Biochem.* 63:777–822 (1994); Astatke, *J. Biol. Chem.* 270:1945–54 (1995)). Converting this amino acid to a Tyr results in a mutant DNA polymerase that does not discriminate against dideoxynucleotides and is highly processive. See copending U.S. application Ser. No. 08/525,087, of Deb K. Chatterjee, filed Sep. 8, 1995, entitled "Mutant DNA Polymerases and the Use Thereof," which is expressly incorporated herein by reference.

Thus, there exists a need in the art to develop thermostable processive DNA polymerases. There also exists a need in the art to obtain wild type or mutant DNA polymerases that are devoid of exonuclease activities and are non-discriminating against dideoxynucleotides.

SUMMARY OF THE INVENTION

The present invention satisfies these needs in the art by providing additional DNA polymerases useful in molecular biology. Specifically, this invention includes a thermostable DNA polymerase having a molecular weight of about 100 kilodaltons. More specifically, the DNA polymerase of the invention is isolated from *Thermotoga neapolitana* (Tne). The Thermotoga species preferred for isolating the DNA polymerase of the present invention was isolated from an African continental solfataric spring (Windberger et al., *Arch. Microbiol.* 151. 506–512, (1989)).

The Tne DNA polymerase of the present invention is extremely thermostable, showing more than 50% of activity after being heated for 60 minutes at 90° C. with or without detergent. Thus, the DNA polymerase of the present invention is more thermostable than Taq DNA polymerase.

The present invention is also directed to cloning a gene encoding a *Thermotoga neapolitana* DNA polymerase enzyme. DNA molecules containing the Tne DNA polymerase gene, according to the present invention, can be transformed and expressed in a host cell to produce a Tne DNA polymerase having a molecular weight of 100 kilodaltons. Any number of hosts may be used to express the Thermotoga DNA polymerase gene of the present invention; including prokaryotic and eukaryotic cells. Preferably, prokaryotic cells are used to express the DNA polymerase of the invention. The preferred prokaryotic hosts according to the present invention is *E. coli*.

The Tne DNA polymerase of the invention may be used in well known DNA sequencing (dideoxy DNA sequencing, cycle DNA sequencing of plasmid DNAs, etc.) and DNA amplification reactions.

The present invention is also directed to mutant thermostable DNA polymerases. More specifically, the mutant DNA polymerases of the invention are derived from *Thermotoga neapolitana* and are substantially reduced or devoid of 3'→5' exonuclease activity, 5'→3' exonuclease activity, or is non-discriminating against dideoxynucleotides. The present invention also relates to mutants having more than one of these properties, and DNA molecules containing the mutant Tne DNA polymerase enzyme genes. These mutants may also be used in well known DNA sequencing and DNA amplification reactions.

BRIEF DESCRIPTION OF THE FIGURES

FIG. 5 shows the nucleotide (SEQ ID NO: 15) and deduced amino acid (SEQ ID NOS: 16–37) sequences, in all 3 reading frames, for the carboxyl terminal portion, including the O-helix region, of the *Thermotoga neapolitana* polymerase gene.

DETAILED DESCRIPTION OF THE PREFERRED EMBODIMENTS

Definitions

Figure 1:
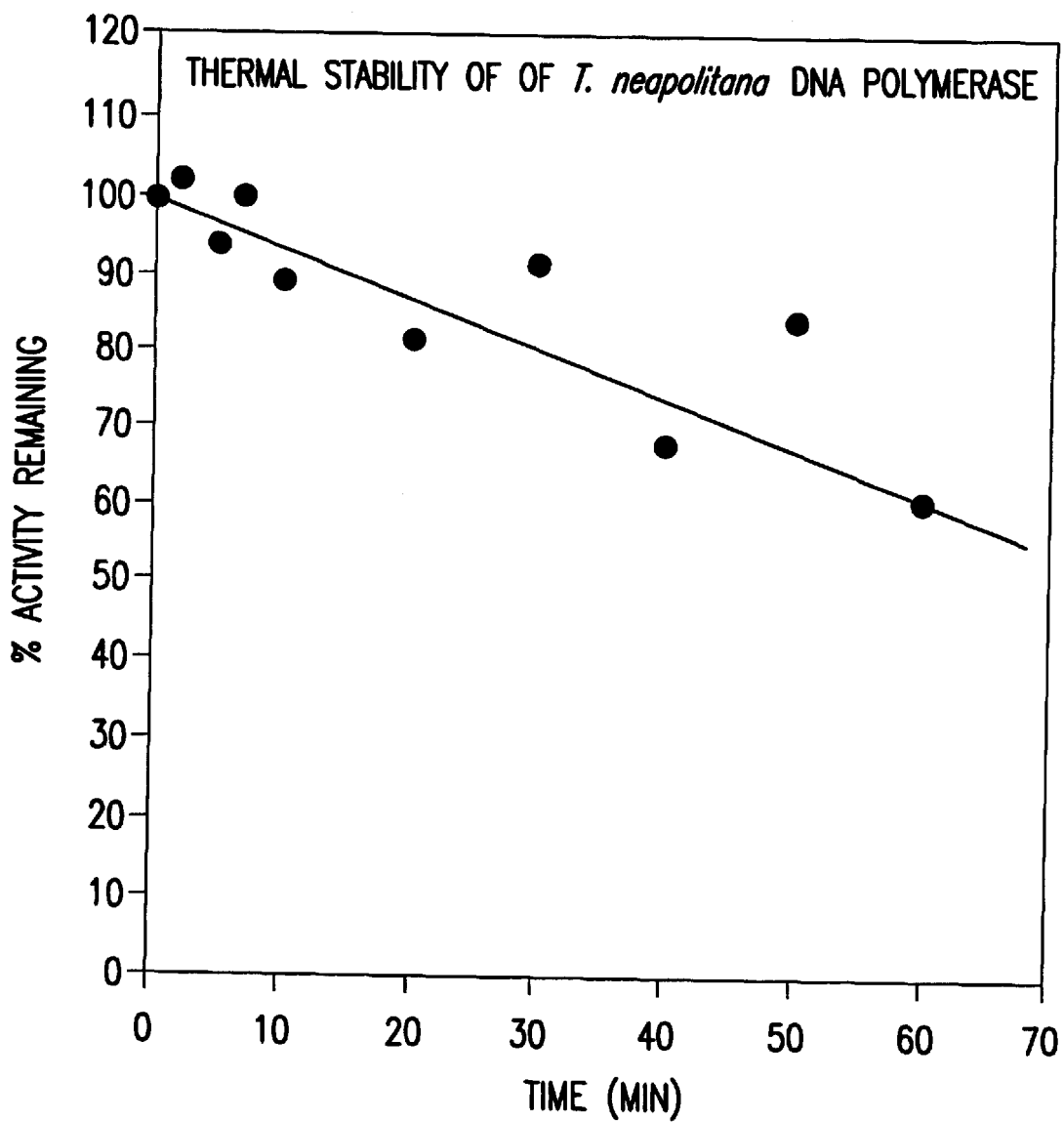
FIG. 1 demonstrates the heat stability of Tne DNA polymerase at 90° C. over time. Crude extract from *Thermotoga neapolitana* cells was used in the assay.
Figure 2:
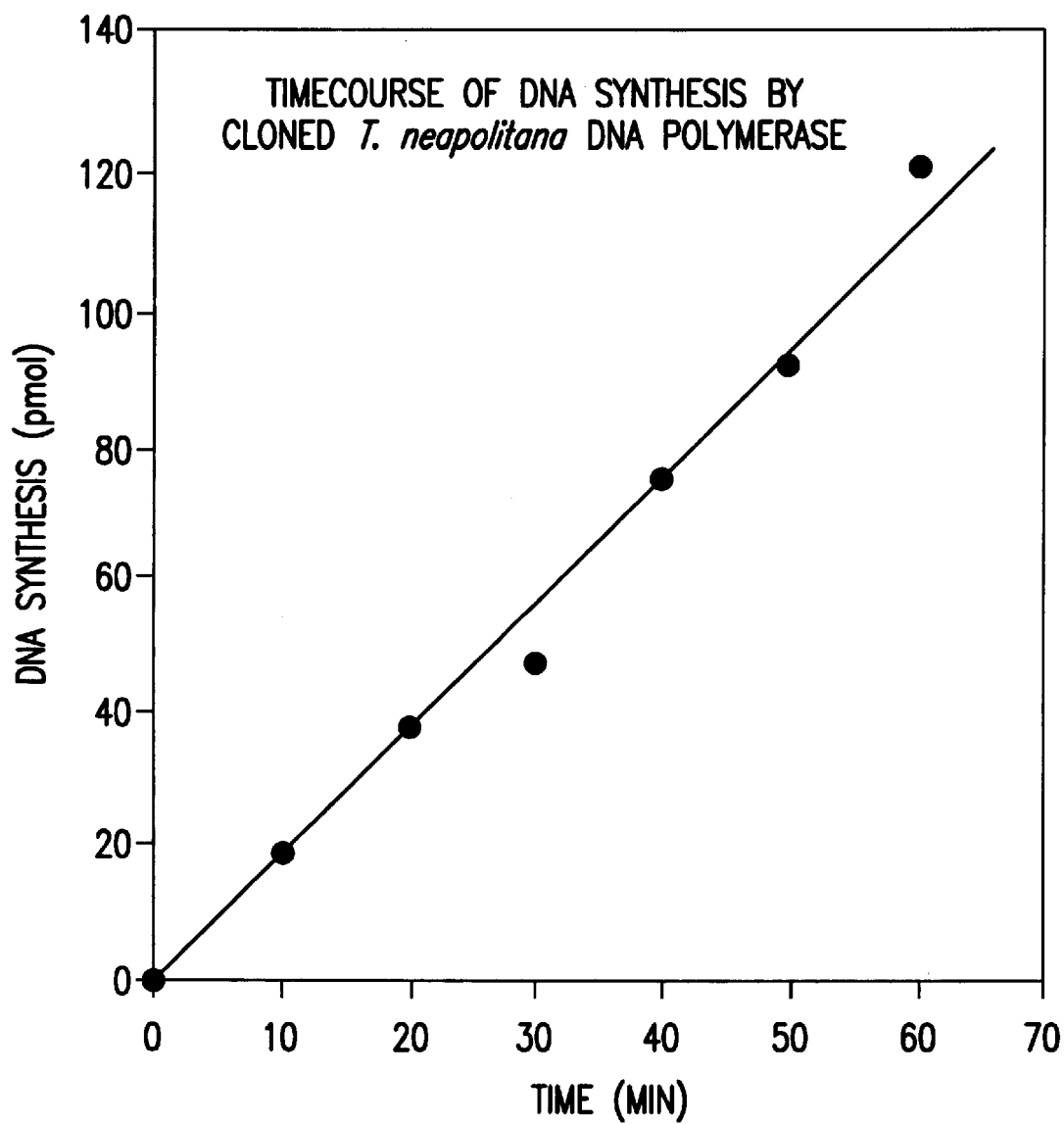
FIG. 2 shows the DNA polymerase activity in crude extracts from an *E. coli* host containing the cloned Tne DNA polymerase gene.
Figure 3:
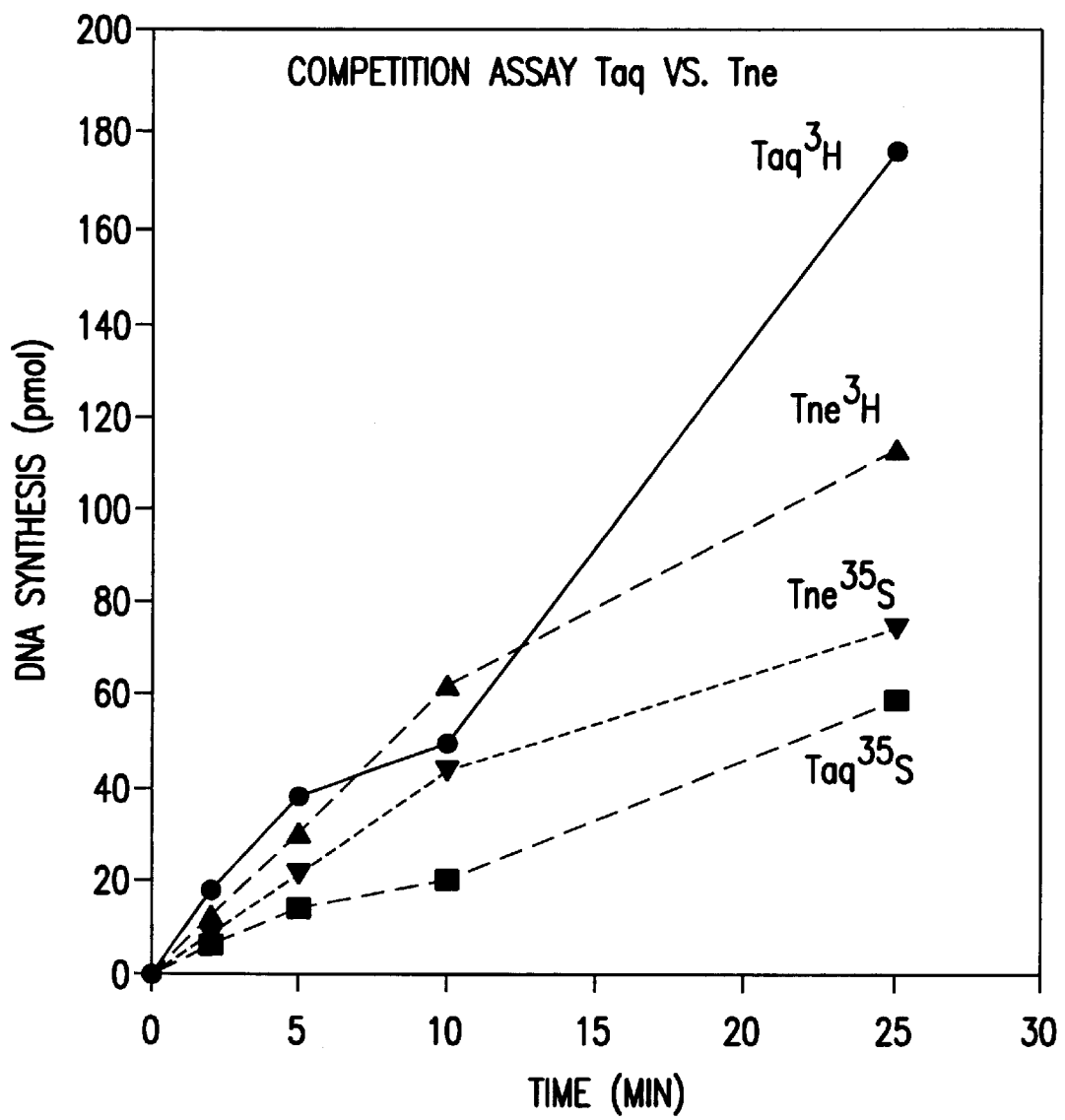
FIG. 3 compares the ability of various DNA polymerases to incorporate radioactive dATP and [αS]dATP. Tne DNA polymerase is more effective at incorporating [αS]dATP than was Taq DNA polymerase.

In the description that follows, a number of terms used in recombinant DNA technology are extensively utilized. In order to provide a clearer and consistent understanding of the specification and claims, including the scope to be given such terms, the following definitions are provided.

Cloning vector. A plasmid, cosmid or phage DNA or other DNA molecule which is able to replicate autonomously in a host cell, and which is characterized by one or a small number of endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences.

Recombinant host. Any prokaryotic or eukaryotic or microorganism which contains the desired cloned genes in an expression vector, cloning vector or any DNA molecule. The term "recombinant host" is also meant to include those host cells which have been genetically engineered to contain the desired gene on the host chromosome or genome.

Host. Any prokaryotic or eukaryotic microorganism that is the recipient of a replicable expression vector, cloning vector or any DNA molecule. The DNA molecule may contain, but is not limited to, a structural gene, a promoter and/or an origin of replication.

Promoter. A DNA sequence generally described as the 5' region of a gene, located proximal to the start codon. At the promoter region, transcription of an adjacent gene(s) is initiated.

Gene. A DNA sequence that contains information necessary for expression of a polypeptide or protein. It includes the promoter and the structural gene as well as other sequences involved in expression of the protein.

Structural gene. A DNA sequence that is transcribed into messenger RNA that is then translated into a sequence of amino acids characteristic of a specific polypeptide.

Operably linked. As used herein means that the promoter is positioned to control the initiation of expression of the polypeptide encoded by the structural gene.

Expression. Expression is the process by which a gene produces a polypeptide. It includes transcription of the gene into messenger RNA (mRNA) and the translation of such mRNA into polypeptide(s).

Substantially Pure. As used herein "substantially pure" means that the desired purified protein is essentially free from contaminating cellular contaminants which are associated with the desired protein in nature. Contaminating cellular components may include, but are not limited to, phosphatases, exonucleases, endonucleases or undesirable DNA polymerase enzymes.

Primer. As used herein "primer" refers to a single-stranded oligonucleotide that is extended by covalent bonding of nucleotide monomers during amplification or polymerization of a DNA molecule.

Template. The term "template" as used herein refers to a double-stranded or single-stranded DNA molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to said template or a portion thereof The newly synthesized DNA molecule, according to the invention, may be equal or shorter in length than the original DNA template. Mismatch incorporation during the synthesis or extension of the newly synthesized DNA molecule may result in one or a number of mismatched base pairs. Thus, the synthesized DNA molecule need not be exactly complementary to the DNA template.

Incorporating. The term "incorporating" as used herein means becoming a part of a DNA molecule or primer.

Amplification. As used herein "amplification" refers to any in vitro method for increasing the number of copies of a nucleotide sequence with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules. As used herein, one amnplification reaction may consist of many rounds of DNA replication. DNA amplification reactions include, for example, polymerase chain reactions (PCR). One PCR reaction may consist of 30 to 100 "cycles" of denaturation and synthesis of a DNA molecule.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA). The term nucleotide includes deoxyribonucleoside triphosphates such as dATP, dCTP, dUTP, dGTP, dTTP, or derivatives thereof. Such derivatives include, for example, dm, [$\alpha$S]dATP and 7-deaza-dGTP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Thermostable. As used herein "thermostable" refers to a DNA polymerase which is resistant to inactivation by heat. DNA polymerases synthesize the formation of a DNA molecule complementary to a single-stranded DNA template by extending a primer in the 5'-to-3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation and thus heat treatment may reduce the DNA polymerase activity to some extent. A thermostable DNA polymerase typically will also have a higher optimum temperature than mesophilic DNA polymerases.

Hybridization. The terms "hybridization" and "hybridizing" refers to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

3'-to-5' Exonuclease Activity. "3'-to-5' exonuclease activity" is an enzymatic activity well known to the art. This activity is often associated with DNA polymerases, and is thought to be involved in a DNA replication "editing" or correction mechanism.

5'-to-3' Exonuclease Activity. "5'-to-3' exonuclease activity" is also an enzymatic activity well known in the art. This activity is often associated with DNA polymerases, such as *E. coli* PolI and PolIII.

A "DNA polymerase substantially reduced in 3'-to-5' exonuclease activity" is defined herein as either (1) a mutated DNA polymerase that has about or less than 10%, or preferably about or less than 1%, of the 3'-to-5' exonuclease activity of the corresponding unmutated, wild-type enzyme, or (2) a DNA polymerase having a 3'-to-5' exonuclease specific activity which is less than about 1 unit/mg protein, or preferably about or less than 0.1 units/mg protein. A unit of activity of 3'-to-5' exonuclease is defined as the amount of activity that solubilizes 10 nmoles of substrate ends in 60 min. at 37° C., assayed as described in the "BRL 1989 Catalogue & Reference Guide", page 5, with HhaI fragments of lambda DNA 3'-end labeled with [$^3$H]dTTP by terminal deoxynucleotidyl transferase (TdT). Protein is measured by the method of Bradford, *Anal. Biochem.* 72:248 (1976). As a means of comparison, natural, wild-type T5-DNAP or T5-DNAP encoded by pTTQ19-T5-2 has a specific activity of about 10 units/mg protein while the DNA polymerase encoded by pTTQ19-T5-2(Exo$^-$) (U.S. Pat. No. 5,270,179) has a specific activity of about 0.0001 units/mg protein, or 0.001% of the specific activity of the unmodified enzyme, a $10^5$-fold reduction.

A "DNA polymerase substantially reduced in 5'-to-3' exonuclease activity" is defined herein as either (1) a mutated DNA polymerase that has about or less than 10%, or preferably about or less than 1%, of the 5'-to-3' exonuclease activity of the corresponding unmutated, wild-type enzyme, or (2) a DNA polymerase having 5'-to-3' exonuclease specific activity which is less than about 1 unit mg protein, or preferably about or less than 0.1 units/mg protein.

Both of these activities, 3'-to-5' exonuclease activity and 5'-to-3' exonuclease activity, can be observed on sequencing gels. Active 5'-to-3' exonuclease activity will produce non-specific ladders in a sequencing gel by removing nucleotides from growing primers. 3'-to-5' exonuclease activity can be measured by following the degradation of radiolabeled primers in a sequencing gel. Thus, the relative amounts of these activities, e.g. by comparing wild-type and mutant polymerases, can be determined from these characteristics of the sequencing gel.

A. Cloning and Expression of Thermotoga neapolitana DNA Polymerase

The Thermotoga DNA polymerase of the invention can be isolated from any strain of Thermotoga which produces a DNA polymerase having the molecular weight of about 100 kilodaltons. The preferred strain to isolate the gene encoding Thermotoga DNA polymerase of the present invention is *Thermotoga neapolitana*. The most preferred *Thermotoga neapolitana* for isolating the DNA polymerase of the invention was isolated from an African continental solfataric spring (Windberger et al., *Arch. Microbiol.* 151:506–512 (1989) and may be obtained from Deutsche Sammalung von Microorganismen und Zellkulturan GmbH (DSM; German Collection of Microorganisms and Cell Culture) Mascheroder Weg lb D-3300 Braunschweig, Federal Republic of Germany, as Deposit No. 5068.

To clone a gene encoding a *Thermotoga neapolitana* DNA polymerase of the invention, isolated DNA which contains the polymerase gene, obtained from *Thermotoga neapolitana* cells, is used to construct a recombinant DNA library in a vector. Any vector, well known in the art, can be used to clone the wild type or mutant *Thermotoga neapolitana* DNA polymerase of the present invention. However, the vector used must be compatible with the host in which the recombinant DNA library will be transformed.

Prokaryotic vectors for constructing the plasmid library include plasmids such as those capable of replication in *E. coli* such as, for example, pBR322, ColE1, pSC101, pUC-vectors (pUC18, pUC19, etc.: In: *Molecular Cloning, A Laboratory Manual*, Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). Bacillus plasmids include pC194, pC221, pC217, etc. Such plasmids are disclosed by Glyczan, T. In: *The Molecular Biology Bacilli*, Academic Press, York (1982), 307–329. Suitable Streptomyces plasmids include pIJ101 (Kendall et al., *J. Bacteriol* 169:4177–4183 (1987)). Pseudomonas plasmids are reviewed by John et al., (Rad. Insec. Dis0. 8:693–704 (1986)), and Igaki, (Jpn. *J. Bacteriol.* 33:729–742 (1978)). Broad-host range plasmids or cosmids, such as pCP13 (Darzins and Chakrabarbary, *J. Bacteriol.* 159:9–18, 1984) can also be used for the present invention. The preferred vectors for cloning the genes of the present invention are prokaryotic vectors. Preferably, pCP13 and pUC vectors are used to clone the genes of the present invention.

The preferred host for cloning the wild type or mutant DNA polymerase genes of the invention is a prokaryotic host. The most preferred prokaryotic host is *E. coli*. However, the wild type or mutant DNA polymerase genes of the present invention may be cloned in other prokaryotic hosts including, but not limited to, Escherichia, Bacillus, Streptomyces, Pseudomonas, Salmonella, Serratia, and Proteus. Bacterial hosts of particular interest include *E. coli* DH10B, which may be obtained from Life Technologies, Inc. (LTI) (Gaithersburg, Md.).

Eukaryotic hosts for cloning and expression of the wild type or mutant DNA polymerases of the present invention include yeast, fungi, and mammalian cells. Expression of the desired DNA polymerase in such eukaryotic cells may require the use of eukaryotic regulatory regions which include eukaryotic promoters. Cloning and expressing the wild type or mutant DNA polymerase gene of the invention in eukaryotic cells may be accomplished by well known techniques using well known eukaryotic vector systems.

Once a DNA library has been constructed in a particular vector, an appropriate host is transformed by well known techniques. Transformed colonies are plated at a density of approximately 200–300 colonies per petri dish. Colonies are then screened for the expression of a heat stable DNA polymerase by transferring transformed *E. coli* colonies to nitrocellulose membranes. After the transferred cells are grown on nitrocellulose (approximately 12 hours), the cells are lysed by standard techniques, and the membranes are then treated at 95° C. for 5 minutes to inactivate the endogenous *E. coli* enzyme. Other temperatures may be used to inactivate the host polymerases depending on the host used and the temperature stability of the DNA polymerase to be cloned. Stable DNA polymerase activity is then detected by assaying for the presence of DNA polymerase activity using well known techniques. Sagner et al., *Gene* 97:119–123 (1991), which is hereby incorporated by reference in its entirety. The gene encoding a DNA polymerase of the present invention can be cloned using the procedure described by Sagner et al., supra.

The recombinant host containing the wild type gene encoding DNA polymerase, *E. coli* DH10B (pUC-Tne), was deposited on Sep. 30, 1994, with the Patent Culture Collection, Northern Regional Research Center, USDA, 1815 North University Street, Peoria, Ill. 61604 U.S.A. as Deposit No. NRRL B-21338.

If the Tne DNA polymerase has 3'-to-5' exonuclease activity, this activity may be reduced, substantially reduced, or eliminated by mutating the Tne DNA polymerase gene. Such mutations include point mutations, frame shift mutations, deletions and insertions. Preferably, the region of the gene encoding the 3'-to-5' exonucleased activity is deleted using techniques well known in the art (Sambrook et al., (1989) in: *Molecular Cloning, A Laboratory Manual* (2nd Ed.), Cold Spring Harbor Laboratory Press, Cold Spring Harbor, N.Y.).

The 3'-to-5' exonuclease activity can be deleted by creating site specific mutants within the 3'→5' exonuclease domain. See infra. In a specific embodiment of the invention $Asp^{322}$ of Tne DNA polymerase was changed to $Ala^{322}$ to substantially reduce 3'-to-5' exonuclease activity.

The 5'→3' exonuclease activity of the Tne DNA polymerase can be reduced or eliminated by mutating the Tne DNA polymerase gene. Such mutations include point mutations, frame shift mutations, deletions, and insertions. Preferably, the region of the gene encoding the 5'→3' exonuclease activity is deleted using techniques well known in the art. In embodiments of this invention, certain conserved amino acids that are associated with the 5'→3' exonuclease activity can be mutated. Examples of these conserved amino acids include $Gly^{37}$. In other embodiments, the entire 5'→3' exonuclease domain of e.g., Tne or Tma polymerase can be deleted by proteolytic cleavage or by genetic engineering. For example, a unique SphI restriction site can be used to obtain a clone devoid of nucleotides encoding the 219 amino terminal amino acids of Tne DNA polymerase. Examples of such a clone are pTTQTne535FY and pTTQTne5FY.

Tne DNA polymerase mutants can also be made to render the polymerase non-discriminating against non-natural nucleotides such as dideoxynucleotides. By way of example, one Tne DNA polymerase mutant having this property substitutes a Tyr for Phe at amino acid 67 as numbered in FIG. 5. Other changes within the O helix of various polymerases such as other point mutations, deletions, and insertions can also be made.

B. Enhancing Expression of *Thermotoga neapolitana* DNA Polymerase

To optimize expression of the wild type or mutant Thermotoga DNA polymerases of the present invention, inducible or constitutive promoters are well known and may be used to express high levels of a polymerase structural gene in a recombinant host. Similarly, high copy number vectors, well known in the art, may be used to achieve high levels of expression. Vectors having an inducible high copy number may also be useful to enhance expression of Thermotoga DNA polymerase in a recombinant host.

To express the desired structural gene in a prokaryotic cell (such as, *E. coli, B. subtilis*, Pseudomonas, etc.), it is necessary to operably link the desired structural gene to a functional prokaryotic promoter. However, the natural *Thermotoga neapolitana* promoter may function in prokaryotic hosts allowing expression of the polymerase gene. Thus, the natural Thermotoga promoter or other promoters may be used to express the DNA polymerase gene. Such other promoters may be used to enhance expression and may either be constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ ($P_L$ and $P_R$), trp, recA, lacZ, lacI, gal, trc, and tac promoters of *E. coli*. The *B. subtilis* promoters include α-amylase (Ulmanen et al., *J. Bacteriol* 162:176–182 (1985)) and Bacillus bacteriophage promoters (Gryczan, T., In: *The Molecular Biology Of Bacilli*, Academic Press, New York (1982)). Streptomyces promoters are described by Ward et al., *Mol. Gen. Genet.* 203:468478 (1986)). Prokaryotic promoters are also reviewed by Glick, *J. Ind. Microbiol.* 1:277–282 (1987); Cenatiempto, Y., *Biochimie* 68:505–516 (1986); and Gottesman, *Ann. Rev. Genet.* 18:415–442 (1984). Expression in a prokaryotic cell also requires the presence of a ribosomal binding site upstream of the gene-encoding sequence. Such ribosomal binding sites are disclosed, for example, by Gold et al., *Ann. Rev. Microbiol.* 35:365404 (1981).

To enhance the expression of Tne DNA polymerase in a eukaryotic cell, well known eukaryotic promoters and hosts may be used. Preferably, however, enhanced expression of Tne DNA polymerase is accomplished in a prokaryotic host. The preferred prokaryotic host for overexpressing this enzyme is *E. coli*.

C. Isolation and Purification of *Thermotoga neapolitana* DNA Polymerase

The enzyme(s) of the present invention (*Thermotoga neapolitana* DNA polymerase, Tne, and mutants thereof) is preferably produced by fermentation of the recombinant host containing and expressing the cloned DNA polymerase gene. However, the wild type and mutant Tne DNA polymerases of the present invention may be isolated from any Thermotoga strain which produces the polymerase of the present invention. Fragments of the Tne polymerase are also included in the present invention. Such fragments include proteolytic fragments and fragments having polymerase activity.

Any nutrient that can be assimilated by *Thermotoga neapolitana* or a host containing the cloned Tne DNA polymerase gene may be added to the culture medium. Optimal culture conditions should be selected case by case according to the strain used and the composition of the culture medium. Antibiotics may also be added to the growth media to insure maintenance of vector DNA containing the desired gene to be expressed. Culture conditions for *Thermotoga neapolitana* have, for example, been described by Huber et al., *Arch. Microbiol.* 144:324–333 (1986). Media formulations are also described in DSM or ATCC Catalogs and Sambrook et al., In: *Molecular Cloning, A Laboratory Manual* (2nd ed.), Cold Spring Harbor Laboratory Press, Cold Spring Harbor, N.Y. (1989).

*Thermotoga neapolitana* and recombinant host cells producing the DNA polymerase of this invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation or centrifugation, the DNA polymerase can be purified by standard protein purification techniques such as extraction, precipitation, chromatography, affinity chromatography, electrophoresis or the like. Assays to detect the presence of the DNA polymerase during purification are well known in the art and can be used during conventional biochemical purification methods to determine the presence of these enzymes.

D. Uses of *Thermotoga neapolitana* DNA polymerase

The wild type and mutant *Thermotoga neapolitana* DNA polymerases (Tne) of the present invention may be used in well known DNA sequencing, DNA labeling, and DNA amplification reactions. Tne DNA polymerase mutants devoid of or substantially reduced in 3'→5' exonuclease activity, devoid of or substantially reduced in 5'→3' exonuclease activity, or containing a $Phe^{67} \rightarrow Tyr^{67}$ mutation are especially useful for DNA sequencing, DNA labeling, and DNA amplification reactions. Moreover, Tne polymerase mutants containing two or more of these properties are also especially useful for DNA sequencing, DNA labeling, on DNA amplification reactions. As is well known, sequencing reactions (dideoxy DNA sequencing and cycle DNA sequencing of plasmid DNA) require the use of DNA polymerases. Dideoxy-mediated sequencing involves the use of a chain-termination technique which uses a specific polymer for extension by DNA polymerase, a base-specific chain terminator and the use of polyacrylamide gels to separate the newly synthesized chain-terminated DNA molecules by size so that at least a part of the nucleotide sequence of the original DNA molecule can be determined. Specifically, a DNA molecule is sequenced by using four separate DNA sequence reactions, each of which contains different base-specific terminators. For example, the first reaction will contain a G-specific terminator, the second reaction will contain a T-specific terminator, the third reaction will contain an A-specific terminator, and a fourth reaction may contain a C-specific terminator. Preferred terminator nucleotides include dideoxyribonucleoside triphosphates (ddNTPs) such as ddATP, ddTTP, ddGTP, and ddCTP. Analogs of dideoxyribonucleoside triphosphates may also be used and are well known in the art.

When sequencing a DNA molecule, ddNTPs lack a hydroxyl residue at the 3' position of the deoxyribose base and thus, although they can be incorporated by DNA polymerases into the growing DNA chain, the absence of the 3'-hydroxy residue prevents formation of a phosphodiester bond resulting in termination of extension of the DNA molecule. Thus, when a small amount of one ddNTP is included in a sequencing reaction mixture, there is competition between extension of the chain and base-specific termination resulting in a population of synthesized DNA molecules which are shorter in length than the DNA template to be sequenced. By using four different ddNTPs in four separate enzymatic reactions, populations of the synthesized DNA molecules can be separated by size so that at least a part of the nucleotide sequence of the original DNA molecule can be determined. DNA sequencing by dideoxynucleotides is well known and is described by Sambrook et al., In: *Molecular Cloning, A Laboratory Manual*, Cold Spring Harbor Laboratory Press, Cold Spring Harbor, N.Y. (1989). As will be readily recognized, the Tne DNA polymerase of the present invention may be used in such sequencing reactions.

As is well known, detectably labeled nucleotides are typically included in sequencing reactions. Any number of labeled nucleotides can be used in sequencing (or labeling) reactions, including, but not limited to, radioactive isotopes, fluorescent labels, chemiluminescent labels, bioluminescent labels, and enzyme labels. It has been discovered that the wild type and mutant Tne DNA polymerase of the present invention may be useful for incorporating $\alpha$S nucleotides ([$\alpha$S]dATP, [$\alpha$S]dTTP, [$\alpha$S]dCTP and [$\alpha$S]dGTP) during sequencing (or labeling) reactions. For example, [$\alpha^{35}$S]dATP, a commonly used detectably labeled nucleotide in sequencing reactions, is incorporated three times more efficiently with the Tne DNA polymerase of the present invention, than with Taq DNA polymerase. Thus, the enzyme of the present invention is particularly suited for sequencing or labeling DNA molecules with [$\alpha^{35}$S]dNTPs.

Polymerase chain reaction (PCR), a well known DNA amplification technique, is a process by which DNA polymerase and deoxyribonucleoside triphosphates are used to amplify a target DNA template. In such PCR reactions, two primers, one complementary to the 3' termini (or near the 3'-termini) of the first strand of the DNA molecule to be amplified, and a second primer complementary to the 3' termini (or near the 3'-termini) of the second strand of the DNA molecule to be amplified, are hybridized to their respective DNA molecules. After hybridization, DNA polymerase, in the presence of deoxyribonucleoside triphosphates, allows the synthesis of a third DNA molecule complementary to the first strand and a fourth DNA molecule complementary to the second strand of the DNA molecule to be amplified. This synthesis results in two double stranded DNA molecules. Such double stranded DNA molecules may then be used as DNA templates for synthesis of additional DNA molecules by providing a DNA polymerase, primers, and deoxyribonucleoside triphosphates. As is well known, the additional synthesis is carried out by "cycling" the original reaction (with excess primers and deoxyribonucleoside triphosphates) allowing multiple denaturing and synthesis steps. Typically, denaturing of double stranded DNA molecules to form single stranded DNA templates is accomplished by high temperatures. The wild type and mutant Thermotoga DNA polymerases of the present invention are heat stable DNA polymerases, and thus will survive such thermal cycling during DNA amplification reactions. Thus, the wild type and mutant Tne polymerases of the invention are ideally suited for PCR reactions, particularly where high temperatures are used to denature the DNA molecules during amplification.

E. Kits

The wild type and mutant *Thermotoga neapolitana* (Tne) DNA polymerases of the invention are suited for the preparation of a kit. Kits comprising the wild type or mutant Tne DNA polymerase(s) may be used for detectably labeling DNA molecules, DNA sequencing, or amplifying DNA molecules by well known techniques, depending on the content of the kit. Such kits may comprise a carrying means being compartmentalized to receive in close confinement one or more container means such as vials, test tubes and the like. Each of such container means comprises components or a mixture of components needed to perform DNA sequencing, DNA labeling, or DNA amplification.

A kit for sequencing DNA may comprise a number of container means. A first container means may, for example, comprise a substantially purified sample of Tne DNA polymerase having the molecular weight of about 100 kilodaltons or a mutant thereof. A second container means may comprise one or a number of types of nucleotides needed to synthesize a DNA molecule complementary to DNA template. A third container means may comprise one or a number different types of dideoxynucleotide triphosphates. In addition to the above container means, additional container means may be included in the kit which comprise one or a number of DNA primers.

A kit used for amplifying DNA will comprise, for example, a first container means comprising a substantially pure mutant or wild type Tne DNA polymerase and one or a number of additional container means which comprise a single type of nucleotide or mixtures of nucleotides. Various primers may or may not be included in a kit for amplifying DNA.

When desired, the kit of the present invention may also include container means which comprise detectably labeled nucleotides which may be used during the synthesis or sequencing of a DNA molecule. One of a number of labels may be used to detect such nucleotides. Illustrative labels include, but are not limited to, radioactive isotopes, fluorescent labels, chemiluminescent labels, bioluminescent labels and enzyme labels.

Having now generally described the invention, the same will be more readily understood through reference to the following Examples which are provided by way of illustration, and are not intended to be limiting of the present invention, unless specified.

EXAMPLE 1

Bacterial Strains And Growth Conditions

*Thermotoga neapolitana* DSM No. 5068 was grown under anaerobic conditions as described in the DSM catalog (addition of resazurin, Na$_2$S, and sulfur granules while sparging the media with nitrogen) at 85° C. in an oil bath from 12 to 24 hours. The cells were harvested by filtering the broth through Whatman #1 filter paper. The supernatant was collected in an ice bath and then centrifuged in a refrigerated centrifuge at 8,000 rpms for twenty minutes. The cell paste was stored at −70° C. prior to total genomic DNA isolation.

*E. coli* strains were grown in 2× LB broth base (Lennox L broth base: GIBCO/BRL) medium. Transformed cells were incubated in SOC (2% tryptone, 0.5% yeast extract, yeast 10 mM NaCl, 2.5M KCl, 20 mM glucose, 10 mM MgCl$_2$, and 10 mM MgSO$_4$ per liter) before plating. When appropriate antibiotic supplements were 20 mg/l tetracycline and 100 mg/l ampicillin. *E. coli* strain DH10B (Lorow et al., *Focus* 12:19–20 (1990)) was used as host strain. Competent DH10B may be obtained from Life Technologies, Inc. (LTI) (Gaithersburg, Md.).

EXAMPLE 2
DNA Isolation

Thermotoga neapolitana chromosomal DNA was isolated from 1.1 g of cells by suspending the cells in 2.5 ml TNE (50 mM Tris-HCl, pH 8.0, 50 mM NaCl, 10 mM EDTA) and treated with 1% SDS for 10 minutes at 37° C. DNA was extracted with phenol by gently rocking the lysed cells overnight at 4° C. The next day, the lysed cells were extracted with chloroform:isoamyl alcohol. The resulting chromosomal DNA was further purified by centrifugation in a CsCl density gradient. Chromosomal DNA isolated from the density gradient was extracted three times with isopropanol and dialyzed overnight against a buffer containing 10 mM Tris-HCl (pH 8.0) and 1 mM EDTA.

EXAMPLE 3
Construction of Genomic Libraries

The chromosomal DNA isolated in Example 2 was used to construct a genomic library in the plasmid pCP13. Briefly, 10 tubes each containing 10 μg of Thermotoga neapolitana chromosomal DNA was digested with 0.01 to 10 units of Sau3Al for 1 hour at 37° C. A portion of the digested DNA was tested in an agarose (1.2%) gel to determine the extent of digestion. Samples with less than 50% digestion were pooled, ethanol precipitated and dissolved in TE. 6.5 μg of partially digested chromosomal DNA was ligated into 1.5 μg of pCP13 cosmid which had been digested with BamHI restriction endonuclease and dephosphorylated with calf intestinal alkaline phosphatase. Ligation of the partially digested Thermotoga DNA and BamHI cleaved pCP13 was carried out with T4 DNA ligase at 22° C. for 16 hours. After ligation, about 1 μg of ligated DNA was packaged using λ-packaging extract (obtained from Life Technologies, Inc., Gaithersburg, Md.). DH10B cells (Life Tech. Inc.) were then infected with 100 μl of the packaged material. The infected cells were plated on tetracycline containing plates. Serial dilutions were made so that approximately 200 to 300 tetracycline resistant colonies were obtained per plate.

EXAMPLE 4
Screening for Clones Expressing Thermotoga neapolitana DNA Polymerase Identification of the Thermotoga neapolitana DNA polymerase gene of the invention was cloned using the method of Sanger et al., Gene 97:119–123 (1991) which reference is herein incorporated in its entirety. Briefly, the E. coli tetracycline resistant colonies from Example 3 were transferred to nitrocellulose membranes and allowed to grow for 12 hours. The cells were then lysed with the fumes of chloroform:toluene (1:1) for 20 minutes and dried for 10 minutes at room temperature. The membranes were then treated at 95° C. for 5 minutes to inactivate the endogenous E. coli enzymes. Surviving DNA polymerase activity was detected by submerging the membranes in 15 ml of polymerase reaction mix (50 mM Tris-HCl (pH 8.8), 1 mM MgCl$_2$, 3 mM β-mercaptoethanol, 10 μM dCTP, dGTP, dTTP, and 15 μCi of 3,000 Ci/mmol [α$^{32}$P]dATP) for 30 minutes at 65° C.

Using autoradiography, three colonies were identified that expressed a Thermotoga neapolitana DNA polymerase. The cells were grown in liquid culture and the protein extract was made by sonication. The presence of the cloned thermostable polymerase was confirmed by treatment at 90° C. followed by measurement of DNA polymerase activity by incorporation of radioactive deoxyribonucleoside triphosphates into acid insoluble DNA. One of the clones, expressing Tne DNA polymerase, contained a plasmid designated pCP13-32 was used for further study.

EXAMPLE 5
Subcloning of Tne DNA polymerase

Figure 4:
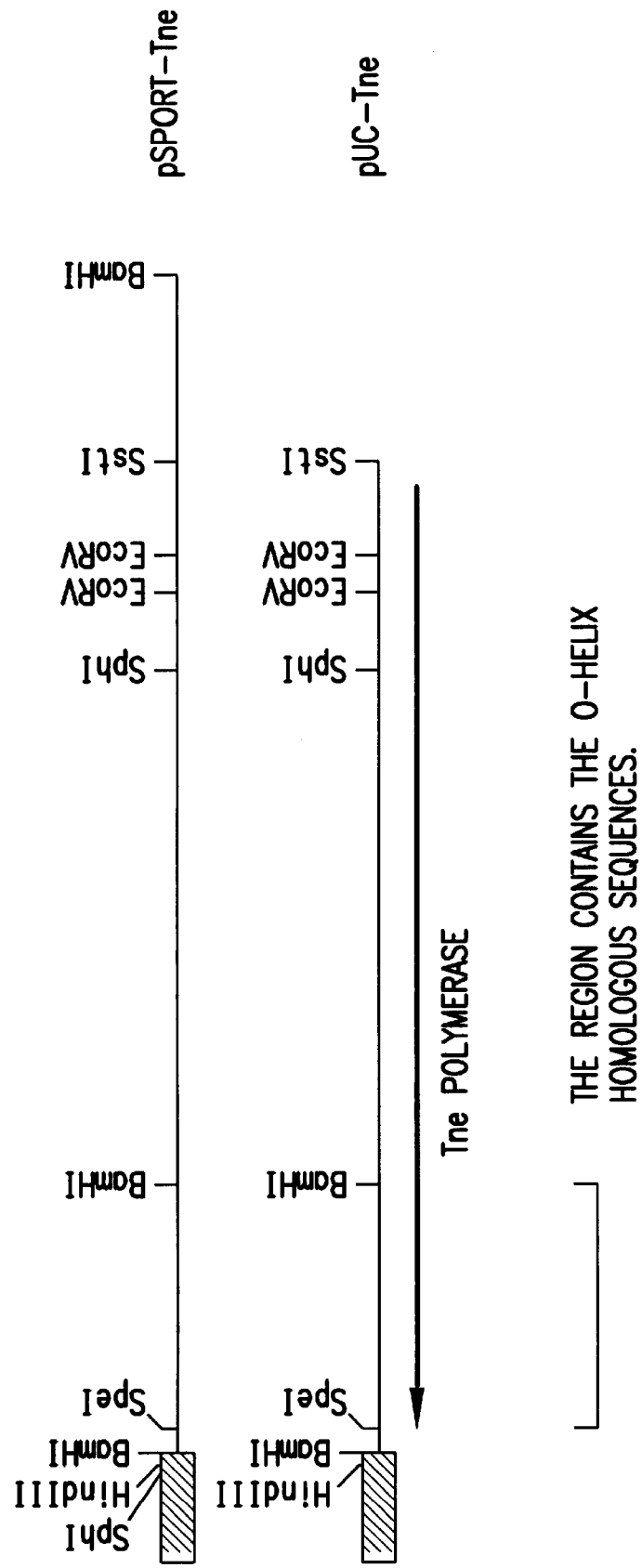
FIG. 4 shows the restriction map of the approximate DNA fragment which contains the Tne DNA polymerase gene in pSport 1 and pUC19. This figure also shows the region containing the O-helix homologous sequences.

Since the pCP13-32 clone expressing the Tne polymerase gene contains about 25 kb of T. neapolitana DNA, we attempted to subclone a smaller fragment of the Tne polymerase gene. The molecular weight of the Tne polymerase purified from E. coli/pCP13-32 was about 100 kd. Therefore, a 2.5–3.0 kb DNA fragment will be sufficient to code for full-length polymerase. A second round of Sau3A partial digestion similar to Example 3 was done using pCP13-32 DNA. In this case, a 3.5 kb region was cut out from the agarose gel, purified by Gene Clean (BIO 101, La Jolla, Calif.) and ligated into plasmid pSport 1 (Life Technologies, Inc.) which had been linearized with BamHI and dephosphoylated with calf intestinal phosphatase. After ligation, DH10B was transformed and colonies were tested for DNA polymerase activity as described in Example 4. Several clones were identified that expressed Tne DNA polymerase. One of the clones (pSport-Tne) containing about 3 kb insert was further characterized. A restriction map of the DNA fragment is shown in FIG. 4. Further, a 2.7 Kb HindIII-SstI fragment was subcloned into pUC 19 to generate pUC19-Tne. E. coli/pUC19-Tne also produced Tne DNA polymerase.

The Tne polymerase clone was sequenced by methods known in the art. The nucleotide sequence obtained of the 5' end prior to the start ATG is shown in SEQ ID NO:1. The nucleotide sequence obtained which encodes the Tne polymerase is shown in SEQ ID NO:2. When SEQ ID NO:2 is translated it does not produce the entire amino acid sequence of the Tne polymerase due to frame shift errors in the nucleotide sequence set forth in SEQ ID NO:2. However, an amino acid sequence of the Tne polymerase was obtained by translating all three reading frames of SEQ ID NO:2, comparing these sequences with known polymerase amino acid sequences, and splicing the Tne polymerase sequence together to form the amino acid sequence set forth in SEQ ID NO:3.

EXAMPLE 6
Purification of Thermotoga neapolitana DNA Polymerase from E. coli Twelve grams of E. coli cells expressing cloned Tne DNA polymerase (DH10B/pSport-Tne) were lysed by sonication (four thirty-second bursts with a medium tip at the setting of nine with a Heat Systems Ultrasonics Inc., model 375 sonicator) in 20 ml of ice cold extraction buffer (50 mM Tris HCl, pH 7.4, 8% glycerol, 5 mM mercaptoethanol, 10 mM NaCl, 1 mM EDTA, 0.5 mM PMSF). The sonicated extract was heated at 80° C. for 15 min. and then cooled in ice for 5 min. 50 mM KCl and PEI (0.4%) was added to remove nucleic acids. The extract was centrifuged for clarification. Ammonium sulfate was added at 60%, the pellet was collected by centrifugation and resuspended in 10 ml of column buffer (25 mM Tris-HCl, pH 7.4, 8% glycerol, 0.5% EDTA, 5 mM 2-mercaptoethanol, 10 mM KCl). A Blue-Sepharose (Pharmacia) column, or preferably a Toso heparin (Tosohaas) column, was washed with 7 column volumes of column buffer and eluted with a 15 column volume gradient of buffer A from 10 mM to 2M KCl. Fractions containing polymerase activity were pooled. The fractions were dialyzed against 20 volumes of column buffer. The pooled fractions were applied to a Toso650Q column (Tosohaas). The column was washed to baseline OD$_{280}$ and elution effected with a linear 10 column volume gradient of 25 mM Tris, pH 7.4, 8% glycerol, 0.5 mM EDTA, 10 mM KCl, 5 mM β-mercaptoethanol to the same buffer plus 650 mM KCl. Active fractions were pooled.

EXAMPLE 7

Characterization of Purified Tne DNA Polymerase

1. Determination of the Molecular Weight of *Thermotoga neapolitana* DNA Polymerase The molecular weight of 100 kilodaltons was determined by electrophoresis in a 12.5% SDS gel by the method of Laemmli, U.K., *Nature* (Lond.) 227:680–685 (1970). Proteins were detected by staining with Coomassie brilliant blue. A 10 kd protein ladder (Life Technologies, Inc.) was used as standard.

2. Method for Measuring Incorporation of $[\alpha^{35}S]$-dATP Relative to $^3$H-dATP Incorporation of $[\alpha S]$dATP was evaluated in a final volume of 500 µl of reaction mix, which was preincubated at 72° C. for five minutes, containing either a [$^3$H]TTP nucleotide cocktail (100 µM each TTP, dATP, dCTP, dGTP with [$^3$H]TTP at 90.3 cpm/pmol), a nucleotide cocktail containing $[\alpha S]$dATP as the only source of dATP (100 µM each $[\alpha S]$dATP, dCTP, dGTP, TTP with $[\alpha^{35}S]$dATP at 235 cpm/pmol), or a mixed cocktail (50 µM $[\alpha S]$dATP, 50 µM dATP, 100 µM TTP, 100 µM dCTP, 100 µM dGTP with [$^{35}\alpha S$]dATP at 118 cpm/pmol and [$^3$H]TTP at 45.2 cpm/pmol). The reaction was initiated by the addition of 0.3 units of *T. neapolitana* DNA polymerase or *T. aquaticus* DNA polymerase. At the times indicated a 25 µl aliquot was removed and quenched by addition of ice cold EDTA to a final concentration of 83 mM. 20 µl aliquots of the quenched reaction samples were spotted onto GF/C filters. Rates of incorporation were compared and expressed as a ratio of *T. neapolitana* to *T. aquaticus*. The incorporation of $[\alpha^{35}S]$ dATP by *T. neapolitana* DNA polymerase was three-fold higher than that of *T. aquaticus* DNA polymerase.

EXAMPLE 8

Reverse Transcriptase Activity $(A)_n:(dT)_{12-18}$ is the synthetic template primer used most frequently to assay for reverse transcriptase activity of DNA polymerases. It is not specific for retroviral-like reverse transcriptase, however, being copied by many prokaryotic and eukaryotic DNA polymerases (Modak and Marcus, *J. Biol. Chem.* 252:11–19 (1977); Gerard et al., *Biochem.* 13:1632–1641 (1974); Spadari and Weissbach, *J. Biol. Chem.* 249:5809–5815 (1974)). $(A)_n:(dT)_{12-18}$ is copied particularly well by cellular, replicative DNA polymerases in the presence of $Mn^{++}$, and much less efficiently in the presence of $Mg^{++}$ (Modak and Marcus, *J. Biol. Chem.* 252:11–19 (1977); Gerard et al., *Biochem.* 13:1632–1641 (1974); Spadari and Weissbach, *J. Biol. Chem.* 249:5809–5815 (1974)). In contrast, most cellular, replicative DNA polymerases do not copy the synthetic template primer $(C)_n:(dG)_{12-18}$ efficiently in presence of either $Mn^{++}$ or $Mg^{++}$, but retroviral reverse transcriptases do. Therefore, in testing for the reverse transcriptase activity of a DNA polymerase with synthetic template primers, the stringency of the test increases in the following manner from least to most stringent: $(A)_n:(dT)_{12-18}$ $(Mn^{++})<(A)_n:(dT)_{12-18}$ $(Mg^{++})<<(C)_n:(dG)_{12-18}$ $(Mn^{++})<(C)_n:(dG)_{12-18}$ $(Mg^{++})$.

The reverse transcriptase activity of *Thermotoga neapolitana* (Tne) DNA polymerase was compared with *Thermus thermophilus* (Tth) DNA polymerase utilizing both $(A)_n:(dT)_{20}$ and $(C)_n:(dG)_{12-18}$. Reaction mixtures (50 µl) with $(A)_n:(dT)_{20}$ contained 50 mM Tris-HCl (pH 8.4), 100 µM $(A)_n$, 100 µM $(dT)_{20}$, and either 40 mM KCl, 6 mM MgCl$_2$, 10 mM dithiothreitol, and 500 µM [$^3$H]dTTP (85 cpm/pmole), or 100 mM KCl, 1 mM MnCl$_2$, and 200 µM [$^3$H]dTTP (92 cpm/pmole). Reaction mixtures (50 µl) with $(C)_n:(dG)_{12-18}$ contained 50 mM Tris-HCl (pH 8.4), 60 µM $(C)_n$, 24 µM $(dG)_{12-18}$, and either 50 mM KCl, 10 mM MgCl$_2$, 10 mM dithiothreitol, and 100 µM [$^3$H]dGTP (132 cpm/pmole), or 100 mM KCl, 0.5 mM MnCl$_2$, and 200 µM [$^3$H]dGTP (107 cpm/pmole). Reaction mixtures also contained either 2.5 units of the Tth DNA polymerase (Perkin-Elmer) or 2.5 units of the Tne DNA polymerase. Incubations were at 45° C. for 10 min followed by 75° C. for 20 min.

The table shows the results of determining the relative levels of incorporation of Tne and Tth DNA polymerase with $(A)_n:(dT)_{20}$ and $(C)_n:(dG)_{12-18}$ in the presence of $Mg^{++}$ and $Mn^{++}$. Tne DNA polymerase appears to be a better reverse transcriptase than Tth DNA polymerase under reaction conditions more specific for reverse transcriptase, i.e., in the presence of $(A)_n:(dT)_{20}$ with $Mg^{++}$ and $(C)_n:(dG)_{12-18}$ with $Mn^{++}$ or $Mg^{++}$.

DNA Polymerase Activity of Tth and Tne DNA Polymerase with $(A)_n:(dT)_{20}$ and $(C)_n:(dG)_{12-18}$

| | DNA Polymerase Activity (pMoles Complementary [$^3$H]dNTP Incorporated) | | | |
|---|---|---|---|---|
| | $(A)_n:(dT)_{20}$ | | $(C)_n:(dG)$ | |
| Enzyme | $Mg^{++}$ | $Mn^{++}$ | $Mg^{++}$ | $Mn^{++}$ |
| Tne | 161.8 | 188.7 | 0.6 | 4.2 |
| Tth | 44.8 | 541.8 | 0 | 0.9 |

EXAMPLE 9

Construction of *Thermotoga Neapolitana* 3'-to-5' Exonuclease Mutant

The amino acid sequence of portions of the Tne DNA polymerase was compared with other known DNA polymerases such as *E. coli* DNA polymerase 1, Taq DNA polymerase, T5 DNA polymerase, and T7 DNA polymerase to localize the regions of 3'-to-5' exonuclease activity, and the dNTP binding domains within the DNA polymerase. We have determined that one of the 3'-to-5' exonuclease domains based on the comparison of the amino acid sequences of various DNA polymerases (Blanco, L., et al. *Gene* 112: 139–144 (1992); Braithwaite and Ito, *Nucleic Acids Res.* 21: 787–802 (1993)) is as follows:

Tne 317 PSFALDLETSS 327 (SEQ ID NO 4)

Pol I 350 PVFAFDTETDS 360 (SEQ ID NO 5; Braithwaite and Ito, supra)

T5 133 GPVAFDSETSA 143 (SEQ ID NO 6; Braithwaite and Ito, supra)

T7 1 MIVSDIEANA 10 (SEQ ID NO 7; Braithwaite and Ito, supra).

As a first step to make the Tne DNA polymerase devoid of 3'→5' exonuclease activity, a 2 kb Sph fragment from pSport-Tne was cloned into M13 mp19 (LTI, Gaithersburg, Md.). The recombinant clone was selected in *E. coil* DH5αF'IQ (LTI, Gaithersburg, Md.). One of the clones with the proper insert was used to isolate uracilated single-stranded DNA by infecting *E. coli* CJ236 (Biorad, California) with the phage particle obtained from *E. coil* DH5aF'IQ. An oligonucleotide, GA CGT TTC AAG CGC TAG GGC AAA AGA (SEQ ID NO. 8) was used to perform site directed mutagenesis. This site-directed mutagenesis converted Asp$^{322}$ (indicated as * above) to Ala$^{322}$. An Eco47III restriction site was created as part of this mutagenesis to facilitate screening of the mutant following mutagenesis. The mutagenesis was performed using a protocol as described in the Biorad manual (1987) except T7 DNA polymerase was used instead of T4 DNA polymerase (USB, Cleveland, Ohio). The mutant clones were screened for the Eco47III restriction site that was created in the mutagenic oligonucleotide. One of the mutants having the created Eco47III restriction site was used for further study.

Figure 6A:
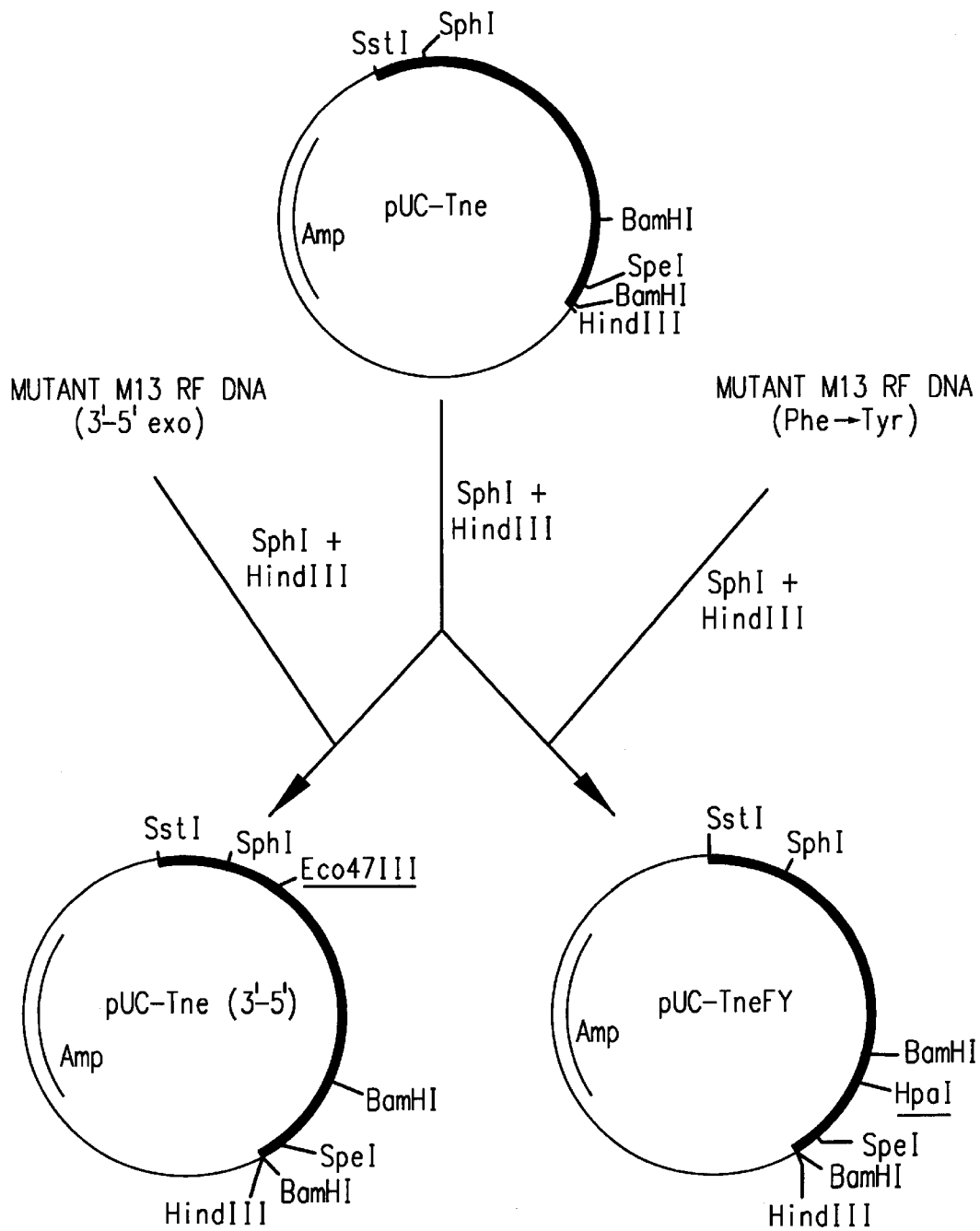
FIG. 6A schematically depicts the construction of plasmids pUC-Tne (3'→5') and pUC-Tne FY.
Figure 6B:
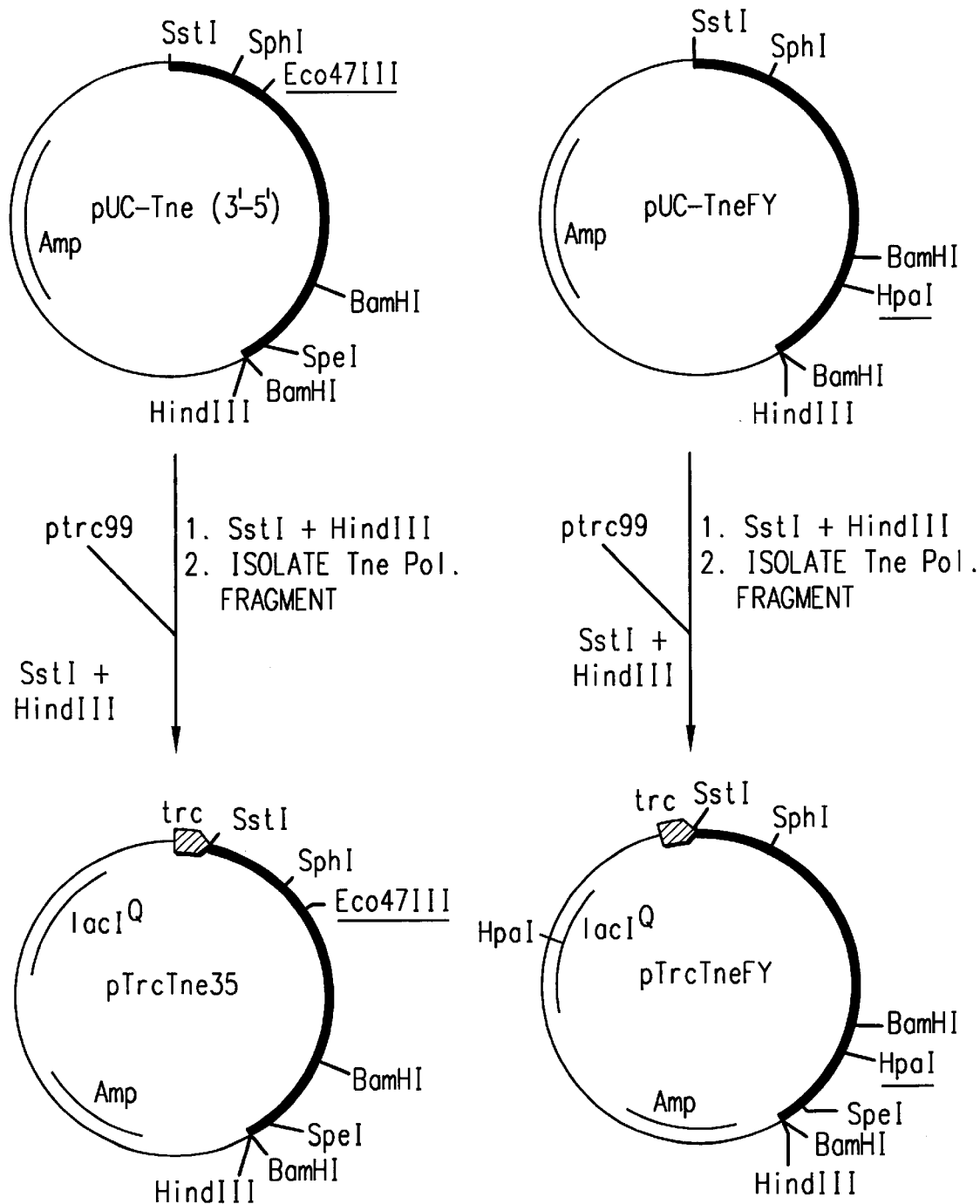
FIG. 6B schematically depicts the construction of plasmids pTrc Tne35 and pTrcTne FY.

To incorporate the 3'-to-5' exonuclease mutation in an expression vector, the mutant phage was digested with SphI and HindIII. A 2 kb fragment containing the mutation was isolated. This fragment was cloned in pUC-Tne to replace the wild type fragment. See FIG. 6A. The desired clone, pUC-Tne (3'→5'), was isolated. The presence of the mutant sequence was confirmed by the presence of the unique Eco47III site. The plasmid was then digested with SstI and HindIII. The entire mutant polymerase gene (2.6 kb) was purified and cloned into SstI and HindIII digested pTrc99 expression vector (Pharmacia, Sweden). The clones were selected in DH10B (LTI, Gaithersburg, Md.). The resulting plasmid was designated pTrcTne35. See FIG. 6B. This clone produced active heat stable DNA polymerase.

EXAMPLE 10
Phenylalanine to Tyrosine Mutant

As discussed supra, the polymerase active site including the dNTP binding domain is usually present at the carboxyl terminal region of the polymerase. The preliminary and partial sequence of the Tne polymerase gene suggests that the amino acids that presumably contact and interact with the dNTPs are present within the 694 bases starting at the internal BamHI site. See FIG. 4. This conclusion is based on homology with a prototype polymerase E. coli polymerase 1. See Polisky et al., J. Biol. Chem. 265:14579–14591 (1990). The sequence of the carboxyl terminal portion of the polymerase gene is shown in FIG. 5 (SEQ ID NOS: 15–16). Based upon this sequence, it is possible to compare the amino acid sequence within the O-helix for various polymerases:

Tne 63 KMVNFSIIYG 72 (SEQ ID NO: 9)
Pol I 758 KAINFGLIYG 767 (SEQ ID NO: 10)
T5 566 KAITFGILYG 575 (SEQ ID NO: 11)
T7 522 KTFIYGFLYG 531 (SEQ ID NO: 12)
Taq 663 KTINFGVLYG 672 (SEQ ID NO: 13)

It was shown that by replacing the phenylalanine residue of Taq DNA polymerases, (indicated as * above) the polymerase becomes non-discriminating against non-natural nucleotides such as dideoxynucleotides. See application Ser. No. 08/525,087 entitled "Mutant DNA Polymerases and Use Thereof" of Deb K. Chatterjee, filed Sep. 8, 1995, specifically incorporated herein by reference. The mutation was based on the assumption that T7 DNA polymerase contains a tyrosine residue in place of the phenylalanine, and T7 DNA polymerase is non-discriminating against dideoxynucleotides. The corresponding residue, Phe$^{762}$ of E. coli PolI is an amino acid that directly interacts with nucleotides. (Joyce and Steitz, Ann. Rev. Biochem. 63:777–822 (1994); Astake, M. J., J. Biol. Chem. 270:1945–1954 (1995)). We prepared a similar mutant of Tne DNA polymerases.

In order to change Phe$^{67}$ of the Tne polymerase to a Tyr$^{67}$ as numbered in FIG. 5, we performed a site-directed mutagenesis using the oligonucleotide GTA TAT TAT AGA GTA GTT AAC CAT CTT TCC A. (SEQ ID NO: 14) As part of this oligonucleotide directed mutagenesis, a HpaI restriction site was created in order to screen mutants easily. The same uracilated single-stranded DNA and mutagenesis procedure described in Example 9 were used for this mutagenesis. Following mutagenesis, the mutants were screened for the HpaI cite. Mutants with the desired HpaI cite were used for further study.

The Phe$^{67}$ to Tyr$^{67}$ mutation was incorporated into pUC-Tne by replacing the wild type SphI-HindIII fragment with the mutant fragment obtained from the mutant phage DNA. The presence of the desired clone, pUC-TneFY, was confirmed by the presence of the unique HpaI site, see FIG. 6A. The entire mutant polymerase gene was subcloned into pTrc99 as an SstI-HindIII as described above in DH10B. The resulting plasmid was designated pTrcTneFY. (FIG. 6B) The clone produced active heat stable polymerase.

EXAMPLE 11
3'-to-5' Exonuclease and Phe$^{67}$→TYR$^{67}$ Double Mutants

Figure 7:
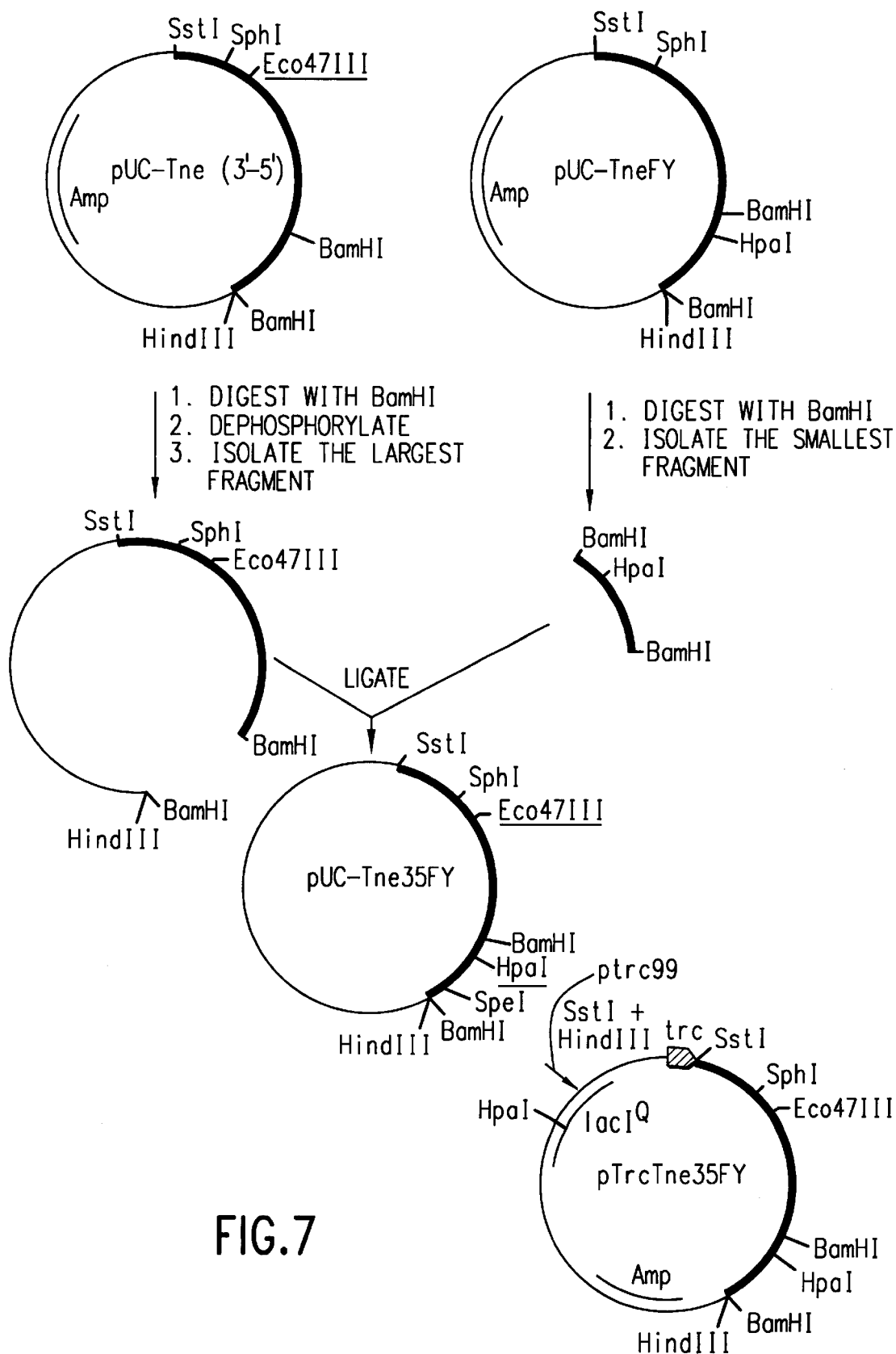
FIG. 7 schematically depicts the construction of plasmid pTrcTne35 FY and pTrcTne535FY.

In order to introduce the 3'→5' exonuclease mutation and the Phe$^{67}$→Tyr$^{67}$ mutation in the same expression vector, pTrc99, it was necessary to first reconstitute both mutations in the pUC-Tne clone. See FIG. 7. Both the pUC-Tne (3'→5') and the pUC-TneFY were digested with BamHI. The digested pUC-Tne (3'→5') was dephosphorylated to avoid recirculation in the following ligations. The resulting fragments were purified on a 1% agarose gel. The largest BamHI fragment (4.4 kb) was purified from pUC-Tne (3'→5') digested DNA and the smallest BamHI fragment (0.8 kb) containing the Phe$^{67}$→Tyr$^{67}$ mutation was purified and ligated to generate pUC-Tne35FY. The proper orientation and the presence of both mutations in the same plasmid was confirmed by Eco47III, HpaI, and SphI-HindIII restriction digests. See FIG. 7.

The entire polymerase containing both mutations was subcloned as a SstI-HindIII fragment in pTrc99 to generate pTrcTne35FY in DH10B. The clone produced active heat stable polymerase.

EXAMPLE 12
3'-to-5' Exonuclease, 5'-to-3' Exonuclease, and Phe$^{67}$→Tyr$^{67}$ Triple Mutants In most of the known polymerases, the 5'-to-3' exonuclease activity is present at the amino terminal region of the polymerase (Ollis, D. L., et al., Nature 313, 762–766, 1985; Freemont, P. S., et al., Proteins 1, 66–73, 1986; Joyce, C. M., Curr. Opin. Struct. Biol. 1, 123–129, 1991). There are some conserved amino acids that are implicated to be responsible for 5'-to-3' exonuclease activity (Gutman and Minton, Nucl. Acids Res. 21, 4406–4407, 1993). See supra. It is known that 5'-to-3' exonuclease domain is dispensable. The best known example is the Klenow fragment of E. coli Pol I. The Klenow fragment is a natural proteolytic fragment devoid of 5'-to-3' exonuclease activity (Joyce, C. M., et al., J. Biol. Chem. 257, 1958–1964, 1990). In order to generate an equivalent mutant for Tne DNA polymerase devoid of 5'-to-3' exonuclease activity we exploited the presence of a unique SphI site present 680 bases from the SstI site. pUC-Tne35FY was digested with HindIII, filled-in with Klenow fragment to generate a blunt-end, and digested with SphI. The 1.9 kb fragment was cloned into an expression vector pTTQ19 (Stark, M. J. R., Gene 51, 255–267, 1987) at the SphI-SmaI sites and was introduced into DH10B. This cloning strategy generated an in-frame polymerase clone with an initiation codon for methionine from the vector. The resulting clone is devoid of 219 amino terminal amino acids of Tne DNA polymerase. This clone is designated as pTTQTne535FY. The clone produced active heat stable polymerase. No exonuclease activity could be detected in the mutant polymerase as evidenced by lack of primer (labeled with radioisotope) degradation in the sequencing reaction. This particular mutant polymerase is highly suitable for DNA sequencing.

EXAMPLE 13

5'-to-3' Exonucleased Deletion and Phe$^{67}$→Tyr$^{67}$ Substitution Mutant

Figure 8:
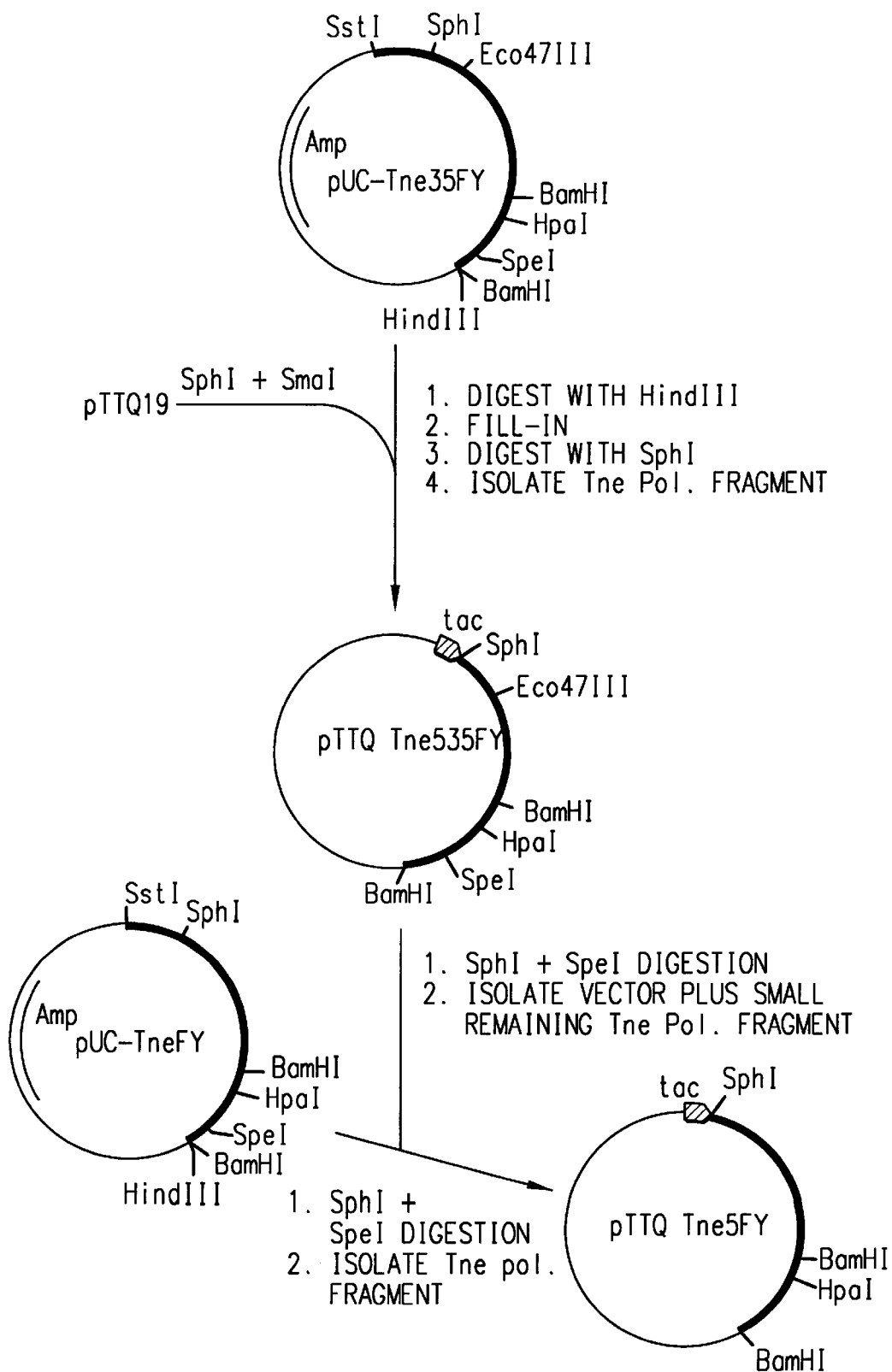
FIG. 8 schematically depicts the construction of plasmid pTTQTne5 FY.

In order to generate the 5'→3' exonuclease deletion mutant of the Tne DNA polymerase Phe$^{67}$→Tyr$^{67}$ mutant, the 1.8 kb SphI-SpeI fragment of pTTQTne35FY was replaced with the identical fragment of pUC-Tne FY. See FIG. 8. A resulting clone, pTTQTne5FY, produced active heat stable DNA polymerase. As measured by the rate of degradation of a labeled primer, this mutant has a modulated, low but detectable, 3'→5' exonuclease activity compared to wild type Tne DNA polymerase. M13 sequencing primer, obtainable from LTI, Gaithersburg, Md., was labeled at the 5' end with [P$^{32}$] ATP and T4 kinase, also obtainable from LTI, Gaithersburg, Md., as described by the manufacturer. The reaction mixtures contained 20 units of either wild-type or mutant Tne DNA polymerase, 0.25 pmol of labeled primer, 20 mM tricine, pH 8.7, 85 mM potassium acetate, 1.2 mM magnesium acetate, and 8% glycerol. Incubation was carried out at 70°C. At various time points, 10 ml aliquots were removed to 5 ml cycle sequencing stop solution and were resolved in a 6% polyacrylamide sequencing gel followed by andoradiography. While the wild-type polymerase degraded the primer in 5 to 15 minutes, it took the mutant polymerase more than 60 minutes for the same amount of degradation of the primer. Preliminary results suggest that this mutant polymerase is able to amplify more than 12 kb of genomic DNA when used in conjunction with Taq DNA polymerase. Thus, the mutant polymerase is suitable for large fragment PCR.

EXAMPLE 14

Purification of the Mutant Polymerases

The purification of the mutant polymerases was done essentially as described in U.S. patent application Ser. No. 08/370,190, filed Jan. 9, 1995, entitled "Cloned DNA Polymerases for *Thermotoga neapolitana*," and as in Example 6, supra, with minor modifications. Specifically, 5 to 10 grams of cells expressing cloned mutant Tne DNA polymerase were lysed by sonication with a Heat Systems Ultrasonic, Inc. Model 375 machine in a sonication buffer comprising 50 mM Tris-HCl, pH 7.4; 8% glycerol; 5 mM 2-mercaptoethanol, 10 mM NaCl, 1 mM EDTA, and 0.5 mM PMSF. The sonication sample was heated at 75° C. for 15 minutes. Following heat treatment, 200 mM NaCl and 0.4% PEI was added to remove nucleic acids. The extract was centrifuged for clarification. Ammonium sulfate was added to 48%, the pellet was resuspended in a column buffer consisting of 25 mM Tris-HCl, pH 7.4; 8% glycerol; 0.5% EDTA; 5 mM 2-mercaptoethanol; 10 mM KCl and loaded on a Heparin agarose column. The column was washed with 10 column volumes using the loading buffer and eluted with a 10 column volume buffer gradient from 10 mM to 1M KCl. Fractions containing polymerase activity were pooled and dialyzed in column buffer as above with the pH adjusted to 7.8. The dialyzed pool of fractions were loaded onto a mono Q column. The column was washed and eluted as described above for the Heparin column. The active fractions are pooled and a unit assay was performed.

The unit assay reaction mixture contained 25 mM TAPS pH 9.3, 2 mM MgCl$_2$, 50 mM KCl, 1 mM DTT, 0.2 mM dNTPs, 500 µg/ml DNAse I treated salmon sperm DNA, 21 mCi/ml [αP$^{32}$] dCTP and various amounts of polymerase in a final volume of 50 ml. After 10 minutes incubation at 70° C., 10 ml of 0.5M EDTA was added to the tube. TCA precipitable counts were measured in GF/C filters using 40 ml of the reaction mixture.

EXAMPLE 15

DNA Sequencing with the Mutant Polymerases

Cycle sequencing reactions using P$^{32}$ end-labeled primers were prepared using wild-type Tne DNA polymerase and each of the three mutants, TneFY, TNE35FY, and Tne535FY. All four of the polymerases produced sequencing ladders. The TneFY mutant gave only a 9 base sequencing ladder when the Taq cycle sequencing reaction conditions were used. Diluting the dideoxynucleotides by a factor of 100 extended the ladder to about 200 bases. The F→Y mutation in the Tne FT polymerase therefore allowed dideoxynucleotides to be incorporated at a much higher frequency than for wild-type polymerase. The TNE35FY mutant demonstrated a similar ability to incorporate dideoxynucleotides. In this case, the sequence extended to beyond 400 bases and the excess P$^{32}$ end-labeled M13/pUC forward 23-Base sequencing primer band remained at the 23-base position in the ladder. The persistence of the 23-base primer band confirmed that the 3'→5' exonuclease activity had been significantly reduced. The Tne535FY mutant performed similarly to the TNE35FY mutant except that the signal intensity increased by at least fivefold. The background was very low and relative band intensities were extremely even, showing no patterns of sequence-dependent intensity variation.

What is claimed is:

1. A mutant *Thermotoga neapolitana* DNA polymerase having at least one mutation selected from the group consisting of (1) a first mutation that substantially reduces or eliminates 3'–5' exonuclease activity of said DNA polymerase, wherein said first mutation is in the 3'–5' exonuclease domain of said DNA polymerase; (2) a second mutation that substantially reduces or eliminates 5'–3' exonuclease activity of said DNA polymerase, wherein said second mutation is in the 5'–3' exonuclease domain of said DNA polymerase; and (3) a third mutation in the O helix of said DNA polymerase resulting in said DNA polymerase becoming non-discriminating against dideoxynucleotides; or a fragment of said mutant *Thermotoga neapolitana* DNA polymerase said fragment having DNA polymerase activity;
   wherein said mutant *Thermotoga neapolitana* DNA polymerase is a Pol I-type DNA polymerase.

2. The mutant *Thermotoga neapolitana* DNA polymerase as claimed in claim 1, wherein said third mutation is a Phe to Tyr substitution at position 67 of the sequence depicted in SEQ ID NO: 16.

3. The mutant *Thermotoga neapolitana* DNA polymerase as claimed in claim 1, wherein said first mutation is a Asp to Ala substitution at position 323 of said DNA polymerase of the sequence depicted in SEQ ID NO: 3.

4. The mutant *Thermotoga neapolitana* DNA polymerase as claimed in claim 1, wherein said mutant polymerase comprises a Phe to Tyr substitution at position 67 of the sequence depicted in SEQ ID NO: 16 and a Asp to Ala substitution at position 322 of the sequence depicted in SEQ ID NO: 3.

5. The mutant *Thermotoga neapolitana* DNA polymerase as claimed in claim 1, wherein said mutant polymerase is devoid of the N-terminal 5'→3' exonuclease domain.

6. The mutant *Thermotoga neapolitana* DNA polymerase as claimed in claim 5, wherein said mutant polymerase is devoid of the 219 N-terminal amino acids of *Thermotoga neapolitana* DNA polymerase.

7. An isolated DNA molecule comprising a DNA sequence encoding a mutant *Thermotoga neapolitana* DNA polymerase having at least one mutation selected from the group consisting of (1) a first mutation that substantially reduces or eliminates 3'–5' exonuclease activity of said DNA polymerase, wherein said first mutation is in the 3'–5' exonuclease domain of said DNA polymerase; (2) a second mutation that substantially reduces or eliminates 5'–3' exonuclease activity of said DNA polymerase, wherein said second mutation is in the 5'–3' exonuclease domain of said DNA polymerase; and (3) a third mutation in the O helix of said DNA polymerase resulting in said DNA polymerase becoming non-discriminating against dideoxynucleotides; or encoding a fragment of said mutant *Thermotoga neapolitana* DNA polymerase said fragment having DNA polymerase activity:
   wherein said mutant *Thermotoga neapolitana* DNA polymerase is a Pol I-type DNA polymerase.

8. The isolated DNA molecule as claimed in claim 7, wherein said DNA molecule is selected from the group consisting of pTrcTne35, pTrcTneFY, pTrcTne35FY, and pTTQTne535FY.

9. The isolated DNA molecule as claimed in claim 7, wherein said DNA molecule further comprises expression control elements.

10. The isolated DNA molecule as claimed in claim 9, wherein said expression control elements comprise an inducible promoter selected from the group consisting of $\lambda P_L$ promoter, a tac promoter, a trp promoter, and a trc promoter.

11. A recombinant host cell comprising a DNA sequence encoding a mutant *Thermotoga neapolitana* DNA polymerase having at least one mutation selected from the group consisting of: (1) a first mutation that substantially reduces or eliminates 3'–5' exonuclease activity of said DNA polymerase, wherein said first mutation is in the 3'–5' exonuclease domain of said DNA polymerase; (2) a second mutation that substantially reduces or eliminates 5'–3' exonuclease activity of said DNA polymerase, wherein said second mutation is in the 5'–3' exonuclease domain of said DNA polymerase; and (3) a third mutation in the O helix of said DNA polymerase resulting in said DNA polymerase becoming non-discriminating against dideoxynucleotides; or encoding a fragment of said mutant *Thermotoga neapolitana* DNA polymerase said fragment having DNA polymerase activity;

wherein said mutant *Thermotoga neapolitana* DNA polymerase is a Pol I-type DNA polymerase.

12. A method of producing a mutant *Thermotoga neapolitana* DNA polymerase, said method comprising:

(a) culturing a cellular host cell comprising a gene encoding a mutant *Thermotoga neapolitana* DNA polymerase having at least one mutation selected from the group consisting of (1) a first mutation that substantially reduces or eliminates 3'–5' exonuclease activity of said DNA polymerase, wherein said first mutation is in the 3'–5' exonuclease domain of said DNA polymerase; (2) a second mutation that substantially reduces or eliminates 5'–3' exonuclease activity of said DNA polymerase, wherein said second mutation is in the 5'–3' exonuclease domain of said DNA polymerase; and (3) a third mutation in the O helix of said DNA polymerase resulting in said DNA polymerase becoming non-discriminating against dideoxynucleotides; or encoding a fragment of said mutant *Thermotoga neapolitana* DNA polymerase said fragment having DNA polymerase activity;

(b) expressing said gene; and (c) isolating said mutant *Thermotoga neapolitana* DNA polymerase from said host cell;

wherein said mutant *Thermotoga neapolitana* DNA polymerase is a Pol I-type DNA polymerase.

13. The method of producing a *Thermotoga neapolitana* DNA polymerase as claimed in claim 12, wherein said host is *E. coli*.

14. A mutant *Thermotoga neapolitana* DNA polymerase having a mutation in the O helix of said DNA polymerase resulting in said DNA polymerase becoming non-discriminating against dideoxynucleotides, or a fragment of said mutant DNA polymerase said fragment having polymerase activity;

wherein said mutant *Thermotoga neapolitana* DNA polymerase is a Pol I-type DNA polymerase.

15. The mutant *Thermotoga neapolitana* DNA polymerase as claimed in claim 14, wherein said mutation is a Phe to Tyr substitution at position 67 of the sequence depicted in SEQ ID NO: 16.

16. The mutant *Thermotoga neapolitana* DNA polymerase as claimed in claim 14, wherein said mutant *Thermotoga neapolitana* DNA polymerase further comprises at least one additional mutation selected from the group consisting of: a first mutation that substantially reduces or eliminates 3'–5' exonuclease activity of said DNA polymerase, wherein said first mutation is in the 3'–5' exonuclease domain of said DNA polymerase and a second mutation that substantially reduces or eliminates 5'–3' exonuclease activity of said DNA polymerase, wherein said second mutation is in the 5'–3' exonuclease domain of said DNA polymerase.

17. The mutant *Thermotoga neapolitana* DNA polymerase as claimed in claim 16, wherein said first mutant is an $Asp^{323}$ to $Ala^{323}$ substitution of the sequence depicted in SEQ ID NO: 3.

18. The mutant *Thermotoga neapolitana* DNA polymerase as claimed in claim 16, wherein said mutant polymerase is devoid of the N-terminal 5' to 3' exonuclease domain.

19. The mutant *Thermotoga neapolitana* DNA polymerase as claimed in claim 18, wherein said mutant polymerase is devoid of the 219 N-terminal amino acids of *Thermotoga neapolitana* DNA polymerase.

20. An isolated DNA molecule comprising a DNA sequence encoding a mutant *Thermotoga neapolitana* DNA polymerase having a mutation in the O helix of said DNA polymerase resulting in said DNA polymerase becoming non-discriminating against dideoxynucleotides, or encoding a fragment of said mutant DNA polymerase said fragment having polymerase activity;

wherein said mutant *Thermotoga neapolitana* DNA polymerase is a Pol I-type DNA polymerase.

21. The isolated DNA molecule as claimed in claim 20, wherein said mutant *Thermotoga neapolitana* DNA polymerase further comprises at least one additional mutation selected from the group consisting of: a first mutation that substantially reduces or eliminates 3'5' exonuclease activity of said DNA polymerase, wherein said first mutation is in the 3'–5' exonuclease domain of said DNA polymerase and a second mutation that substantially reduces or eliminates 5'–3' exonuclease activity of said DNA polymerase, wherein said second mutation is in the 5'–3' exonuclease domain of said DNA polymerase.

22. The isolated DNA molecule as claimed in claim 20, wherein said DNA molecule further comprises expression control elements.

23. The isolated DNA molecule as claimed in claim 22, wherein said expression control elements comprise an inducible promoter selected from the group consisting of a $\lambda P_L$ promoter, a tac promoter, a trp promoter, and a trc promoter.

24. A recombinant host cell comprising a DNA sequence encoding a mutant *Thermotoga neapolitana* DNA polymerase having a mutation in the O helix of said DNA polymerase resulting in said DNA polymerase becoming non-discriminating against dideoxynucleotides, or encoding a fragment of said mutant DNA polymerase said fragment having polymerase activity;

wherein said mutant *Thermotoga neapolitana* DNA polymerase is a Pol I-type DNA polymerase.

25. The recombinant host cell as claimed in claim 24, wherein said mutant *Thermotoga neapolitana* DNA polymerase further comprises at least one additional mutation selected from the group consisting of: a first mutation that substantially reduces or eliminates 3'–5' exonuclease activity of said DNA polymerase, wherein said first mutation is in the 3'–5' exonuclease domain of said DNA polymerase and a second mutation that substantially reduces or eliminates 5'–3' exonuclease activity of said DNA polymerase, wherein said second mutation is in the 5'–3' exonuclease domain of said DNA polymerase.

26. A method of producing a mutant *Thermotoga neapolitana* DNA polymerase, said method comprising:

(a) culturing a cellular host cell comprising a gene encoding a mutant *Thermotoga neapolitana* DNA polymerase having a mutation in the O helix of said DNA polymerase resulting in said DNA polymerase becoming non-discriminating against dideoxynucleotides, or encoding a fragment of said mutant DNA polymerase said fragment having polymerase activity;

(b) expressing said gene; and (c) isolating said mutant *Thermotoga neapolitana* DNA polymerase from said host cell;

wherein said mutant *Thermotoga neapolitana* DNA polymerase is a Pol I-type DNA polymerase.

27. The method of producing a mutant *Thermotoga neapolitana* DNA polymerase as claimed in claim 26, wherein said mutant *Thermotoga neapolitana* DNA polymerase further comprises at least one additional mutation selected from the group consisting of: a first mutation that substantially reduces or eliminates 3'–5' exonuclease activity of said DNA polymerase, wherein said first mutation is in the 3'–5' exonuclease domain of said DNA polymerase and a second mutation that substantially reduces or eliminates 5'–3' exonuclease activity of said DNA polymerase, wherein said second mutation is in the 5'–3' exonuclease domain of said DNA polymerase.

28. The method of producing a *Thermotoga neapolitana* DNA polymerase as claimed in claim 26, wherein said host cell is *E. coli*.

29. A mutant *Thermotoga neapolitana* DNA polymerase having a mutation that substantially reduces or eliminates 3'–5' exonuclease activity of said polymerase, wherein said mutation is in the 3'–5' exonuclease domain of said polymerase, and further wherein said mutant *Thermotoga neapolitana* DNA polymerase is a Pol I-type DNA polymerase.

30. An isolated DNA molecule comprising a DNA sequence encoding a mutant *Thermotoga neapolitana* DNA polymerase having a mutation that substantially reduces or eliminates 3'–5' exonuclease activity of said polymerase, wherein said mutation is in the 3'–5' exonuclease domain of said polymerase, and further wherein said mutant *Thermotoga neapolitana* DNA polymerase is a Pol I-type DNA polymerase.

31. The isolated DNA molecule as claimed in claim 30, wherein said DNA molecule further comprises expression control sequences.

32. A recombinant host cell comprising a DNA sequence encoding a mutant *Thermotoga neapolitana* DNA polymerase having a mutation that substantially reduces or eliminates 3'–5' exonuclease activity of said polymerase, wherein said mutation is in the 3'–5' exonuclease domain of said polymerase, and further wherein said mutant *Thermotoga neapolitana* DNA polymerase is a Pol I-type DNA polymerase.

33. A method of producing a mutant *Thermotoga neapolitana* DNA polymerase, said method comprising:

(a) culturing a host cell comprising a gene encoding a mutant *Thermotoga neapolitana* DNA polymerase having a mutation that substantially reduces or eliminates 3'–5' exonuclease activity of said polymerase, wherein said mutation is in the 3'–5' exonuclease domain of said polymerase, and further wherein said mutant *Thermotoga neapolitana* DNA polymerase is a Pol I-type DNA polymerase;

(b) expressing said gene; and (c) isolating said mutant *Thermotoga neapolitana* DNA polymerase from said host cell.

34. A mutant *Thermotoga neapolitana* DNA polymerase having a mutation that substantially reduces or eliminates 5'–3' exonuclease activity of said polymerase, wherein said mutation is in the 5'–3' exonuclease domain of said polymerase, and further wherein said mutant *Thermotoga neapolitana* DNA polymerase is a Pol I-type DNA polymerase.

35. An isolated DNA molecule comprising a DNA sequence encoding a mutant *Thermotoga neapolitana* DNA polymerase having a mutation that substantially reduces or eliminates 5'–3' exonuclease activity of said polymerase, wherein said mutation is in the 5'–3' exonuclease domain of said polymerase, and further wherein said mutant *Thermotoga neapolitana* DNA polymerase is a Pol I-type DNA polymerase.

36. The isolated DNA molecule as claimed in claim 30, wherein said DNA molecule further comprises expression control sequences.

37. A recombinant host cell comprising a DNA sequence encoding a mutant *Thermotoga neapolitana* DNA polymerase having a mutation that substantially reduces or eliminates 5'–3' exonuclease activity of said polymerase, wherein said mutation is in the 5'–3' exonuclease domain of said polymerase, and further wherein said mutant *Thermotoga neapolitana* DNA polymerase is a Pol I-type DNA polymerase.

38. A method of producing a mutant *Thermotoga neapolitana* DNA polymerase, said method comprising:

(a) culturing a host cell comprising a gene encoding a mutant *Thermotoga neapolitana* DNA polymerase having a mutation that substantially reduces or eliminates 5'–3' exonuclease activity of said polymerase, wherein said mutation is in the 5'–3' exonuclease domain of said polymerase, and further wherein said mutant *Thermotoga neapolitana* DNA polymerase is a Pol I-type DNA polymerase;

(b) expressing said gene; and (c) isolating said mutant *Thermotoga neapolitana* DNA polymerase from said host cell.

* * * * *

UNITED STATES PATENT AND TRADEMARK OFFICE
CERTIFICATE OF CORRECTION

PATENT NO. : 5,939,301

DATED : August 17, 1999

INVENTOR(S) : Hughes, Jr. et al.

It is certified that error appears in the above-identified patent and that said Letters Patent is hereby corrected as shown below:

Column 42, line 54, at claim 7, after "activity", please delete ":" and insert therein --;--.

Column 44, line 29, at claim 21, please delete "3'5'" and insert therein --3'-5'--.

Signed and Sealed this

Twenty-ninth Day of February, 2000

Attest:

Q. TODD DICKINSON

Attesting Officer

Commissioner of Patents and Trademarks

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
      (A) LENGTH: 23 base pairs
      (B) TYPE: nucleic acid
      (C) STRANDEDNESS: both
      (D) TOPOLOGY: both (vi) ORIGINAL SOURCE:
      (A) ORGANISM: Thermotoga neapolitana (xi) SEQUENCE DESCRIPTION: SEQ ID NO: 1:

GAGCTCACGG GGGATGCAGG AAA                                              23

(2) INFORMATION FOR SEQ ID NO: 2:

(i) SEQUENCE CHARACTERISTICS:
        (A) LENGTH: 1310 base pairs
        (B) TYPE: nucleic acid
        (C) STRANDEDNESS: both
        (D) TOPOLOGY: linear (vi) ORIGINAL SOURCE:
        (A) ORGANISM: Thermotoga neapolitana (xi) SEQUENCE DESCRIPTION: SEQ ID NO: 2:

ATGGCGAGAC TATTTCTCTT TGATGGCACA GCCCTGGCCT ACAGGGCATA TTACGCCCTC       60

GACAGATCCC TTTCCACATC CACAGGAATT CCAACGAACG CCGTCTATGG CGTTGCCAGG      120

ATGCTCGTTA AATTCATTAA GGAACACATT ATACCCGAAA AGGACTACGC GGCTGTGGCC      180

TTCGACAAGA AGGCAGCGAC GTTCAGACAC AAACTGCTCG TAAGCGACAA GGCGCAAAGG      240

CCAAAGACGC CGGTCTTCT AGTTCAGCAG CTACCTTACA TCAAGCGGCT GATAGAAGCT       300

CTTGGTTTCA AAGTGCTGGA GCTGGAAGGG TACGAAGCAG ACGATATCAT CGCCACGCTT      360

GCAGCAAAGG GCTGCACGTT TTTTGATGAG ATTTTCATAA TAACCGGTGA CAAGGATATG      420

CTTCAACTTG TAAACGAGAA GATAAAGGTC TGGAGAATCG TCAAGGGGAT ATCGGATCTT      480

GAGCTTTACG ATTCGAAAAA GGTGAAAGAA AGATACGGTG TGGAACCACA TCAGATACCG      540

GATCTTCTAG CACTGACGGG AGACGACATA GACAACATTC CCGGTGTAAC GGGAATAGGT      600

GAAAAGACCG CTGTACAGCT TCTCGGCAAG TATAGAAATC TTGAATACAT TCTGGAGCAT      660

GCCCGTGAAC TCCCCCAGAG AGTGAGAAAG GCTCTCTTGA GAGACAGGGA AGTTGCCATC      720

CTCAGTAAAA AACTTGCAAC TCTGGTGACG AACGCACCTG TTGAAGTGGA CTGGGAAGAG      780

ATGAAATACA GAGGATACGA CAAGAGAAAA CTACTTCCGA TATTGAAAGA ACTGGAGTTT      840

GCTTCCATCA TGAAGGAACT TCAACTGTAC GAAGAAGCAG AACCCACCGG ATACGAAATC      900

GTGAAGGATC ATAAGACCTT CGAAGATCTC ATCGAAAAGC TGAAGGAGGT TCCATCTTTT      960

GCCCTGGACC TTGAAACGTC CTCCTTGGAC CCGTTCAACT GTGAGATAGT CGGCATCTCC     1020

GTGTCGTTCA AACCGAAAAC AGCTTATTAC ATTCCACTTC ATCACAGAAA CGCCCACAAT     1080

CTTGATGAAA CACTGGTGCT GTCGAAGTTG AAAGAGATCC TCGAAGACCC GTCTTCGAAG     1140

ATTGTGGGTC AGAACCTGAA GTACGACTAC AAGGTTCTTA TGGTAAAGGG TATATCGCCA     1200

GTTTATCCGC ATTTTGACAC GATGATAGCT GCATATTTGC TGGAGCCAAA CGAGAAAAAA     1260

TTCAATCTCG AAGATCTGTC TTTGAAATTT CTCGGATACA AAATGACGTC              1310

(2) INFORMATION FOR SEQ ID NO: 3:

(i) SEQUENCE CHARACTERISTICS:
        (A) LENGTH: 436 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Thermotoga neapolitana (xi) SEQUENCE DESCRIPTION: SEQ ID NO: 3:

Met Ala Arg Leu Phe Leu Phe Asp Gly Thr Ala Leu Ala Tyr Arg Ala
    1               5                   10                  15

```
Tyr Tyr Ala Leu Asp Arg Ser Leu Ser Thr Ser Thr Gly Ile Pro Thr
         20                  25                  30

Asn Ala Val Tyr Gly Val Ala Arg Met Leu Val Lys Phe Ile Lys Glu
             35                  40                  45

His Ile Ile Pro Glu Lys Asp Tyr Ala Ala Val Ala Phe Asp Lys Lys
     50                  55                  60

Ala Ala Thr Phe Arg His Lys Leu Leu Val Ser Asp Lys Ala Gln Arg
 65                  70                  75                  80

Pro Lys Thr Pro Ala Leu Leu Val Gln Gln Leu Pro Tyr Ile Lys Arg
                 85                  90                  95

Leu Ile Glu Ala Leu Gly Phe Lys Val Leu Glu Leu Glu Gly Tyr Glu
             100                 105                 110

Ala Asp Asp Ile Ile Ala Thr Leu Ala Ala Lys Gly Cys Thr Phe Phe
             115                 120                 125

Asp Glu Ile Phe Ile Ile Thr Gly Asp Lys Asp Met Leu Gln Leu Val
     130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
             165                 170                 175

His Gln Ile Pro Asp Leu Leu Ala Leu Thr Gly Asp Asp Ile Asp Asn
             180                 185                 190

Ile Pro Gly Val Thr Gly Ile Gly Glu Lys Thr Ala Val Gln Leu Leu
         195                 200                 205

Gly Lys Tyr Arg Asn Leu Glu Tyr Ile Leu Glu His Ala Arg Glu Leu
     210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
             245                 250                 255

Asp Trp Glu Glu Met Lys Tyr Arg Gly Tyr Asp Lys Arg Lys Leu Leu
             260                 265                 270

Pro Ile Leu Lys Glu Leu Glu Phe Ala Ser Ile Met Lys Glu Leu Gln
             275                 280                 285

Leu Tyr Glu Glu Ala Glu Pro Thr Gly Tyr Glu Ile Val Lys Asp His
     290                 295                 300

Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
             325                 330                 335

Val Gly Ile Ser Val Ser Phe Lys Pro Lys Thr Ala Tyr Tyr Ile Pro
             340                 345                 350

Leu His His Arg Asn Ala His Asn Leu Asp Glu Thr Leu Val Leu Ser
     355                 360                 365

Lys Leu Lys Glu Ile Leu Glu Asp Pro Ser Ser Lys Ile Val Gly Gln
     370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
                 405                 410                 415

Asn Glu Lys Lys Phe Asn Leu Glu Asp Leu Ser Leu Lys Phe Leu Gly
             420                 425                 430

Tyr Lys Met Thr
             435
```

(2) INFORMATION FOR SEQ ID NO: 4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Pro Ser Phe Ala Leu Asp Leu Glu Thr Ser Ser
1               5                   10
```

(2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Pro Val Phe Ala Phe Asp Thr Glu Thr Asp Ser
1               5                   10
```

(2) INFORMATION FOR SEQ ID NO: 6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Gly Pro Val Ala Phe Asp Ser Glu Thr Ser Ala
1               5                   10
```

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Met Ile Val Ser Asp Ile Glu Ala Asn Ala
1               5                   10
```

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: both
        (D) TOPOLOGY: both (xi) SEQUENCE DESCRIPTION: SEQ ID NO: 8:

```
GACGTTTCAA GCGCTAGGGC AAAAGA                                     26
```

(2) INFORMATION FOR SEQ ID NO: 9:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 9:

Lys Met Val Asn Phe Ser Ile Ile Tyr Gly
 1               5                  10

(2) INFORMATION FOR SEQ ID NO: 10:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Lys Ala Ile Asn Phe Gly Leu Ile Tyr Gly
 1               5                  10

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Lys Ala Ile Thr Phe Gly Ile Leu Tyr Gly
 1               5                  10

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Lys Thr Phe Ile Tyr Gly Phe Leu Tyr Gly
 1               5                  10

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Lys Thr Ile Asn Phe Gly Val Leu Tyr Gly
 1               5                  10

(2) INFORMATION FOR SEQ ID NO: 14:

```
    (i) SEQUENCE CHARACTERISTICS:
        (A) LENGTH: 31 base pairs
        (B) TYPE: nucleic acid
        (C) STRANDEDNESS: both
        (D) TOPOLOGY: both (xi) SEQUENCE DESCRIPTION: SEQ ID NO: 14:

GTATATTATA GAGTAGTTAA CCATCTTTCC A                                    31

(2) INFORMATION FOR SEQ ID NO: 15:

(i) SEQUENCE CHARACTERISTICS:
        (A) LENGTH: 694 base pairs
        (B) TYPE: nucleic acid
        (C) STRANDEDNESS: double
        (D) TOPOLOGY: both (ix) FEATURE:
        (A) NAME/KEY: CDS
        (B) LOCATION:2..694

(xi) SEQUENCE DESCRIPTION: SEQ ID NO: 15:

G GAT CCA GAC TGG TGG ATC GTC AGT GCG GAT TAT TCC CAA ATA GAA         46
  Asp Pro Asp Trp Trp Ile Val Ser Ala Asp Tyr Ser Gln Ile Glu
  1               5                  10                  15

CTC AGA ATC CTC GCT CAT CTC AGT GGT GAT GAG AAC CTT GTG AAG GCC       94
Leu Arg Ile Leu Ala His Leu Ser Gly Asp Glu Asn Leu Val Lys Ala
                    20                  25                  30

TTC GAG GAG GGC ATC GAT GTG CAC ACC TTG ACT GCC TCC AGG ATC TAC      142
Phe Glu Glu Gly Ile Asp Val His Thr Leu Thr Ala Ser Arg Ile Tyr
                35                  40                  45

AAC GTA AAG CCA GAA GAA GTG AAC GAA GAA ATG CGA CGG GTT GGA AAG      190
Asn Val Lys Pro Glu Glu Val Asn Glu Glu Met Arg Arg Val Gly Lys
            50                  55                  60

ATG GTG AAC TTC TCT ATA ATA TAC GGT GTC ACA CCG TAC GGT CTT TCT      238
Met Val Asn Phe Ser Ile Ile Tyr Gly Val Thr Pro Tyr Gly Leu Ser
        65                  70                  75

GTG AGA CTT GGA ATA CCG GTT AAA GAA GCA GAA AAG ATG ATT ATC AGC      286
Val Arg Leu Gly Ile Pro Val Lys Glu Ala Glu Lys Met Ile Ile Ser
    80                  85                  90                  95

TAT TTC ACA CTG TAT CCA AAG GTG CGA AGC TAC ATC CAG CAG GTT GTT      334
Tyr Phe Thr Leu Tyr Pro Lys Val Arg Ser Tyr Ile Gln Gln Val Val
                    100                 105                 110

GCA GAG GCA AAA GAG AAG GGC TAC GTC AGG ACT CTC TTT GGA AGA AAA      382
Ala Glu Ala Lys Glu Lys Gly Tyr Val Arg Thr Leu Phe Gly Arg Lys
                115                 120                 125

AGA GAT ATT CCC CAG CTC ATG GCA AGG GAC AAG AAC ACC CAG TCC GAA      430
Arg Asp Ile Pro Gln Leu Met Ala Arg Asp Lys Asn Thr Gln Ser Glu
            130                 135                 140

GGC GAA AGA ATC GCA ATA AAC ACC CCC ATT CAG GGA ACT GCG GCA GAT      478
Gly Glu Arg Ile Ala Ile Asn Thr Pro Ile Gln Gly Thr Ala Ala Asp
        145                 150                 155

ATA ATA AAA TTG GCT ATG ATA GAT ATA GAC GAG GAG CTG AGA AAA AGA      526
Ile Ile Lys Leu Ala Met Ile Asp Ile Asp Glu Glu Leu Arg Lys Arg
160                 165                 170                 175

AAC ATG AAA TCC AGA ATG ATC ATT CAG GTT CAT GAC GAA CTG GTC TTC      574
Asn Met Lys Ser Arg Met Ile Ile Gln Val His Asp Glu Leu Val Phe
                    180                 185                 190

GAG GTT CCC GAT GAG GAA AAA GAA GAA CTA GTT GAT CTG GTG AAG AAC      622
Glu Val Pro Asp Glu Glu Lys Glu Glu Leu Val Asp Leu Val Lys Asn
                195                 200                 205

AAA ATG ACA AAT GTG GTG AAA CTC TCT GTG CCT CTT GAG GTT GAC ATA      670
Lys Met Thr Asn Val Val Lys Leu Ser Val Pro Leu Glu Val Asp Ile
```

```
                210             215             220
AGC ATC GGA AAA AGC TGG TCT TGA                                              694
Ser Ile Gly Lys Ser Trp Ser
    225             230
```

(2) INFORMATION FOR SEQ ID NO: 16:

(i) SEQUENCE CHARACTERISTICS:
        (A) LENGTH: 230 amino acids
        (B) TYPE: amino acid
        (D) TOPOLOGY: linear (ii) MOLECULE TYPE: protein (xi) SEQUENCE DESCRIPTION: SEQ ID NO: 16:

```
Asp Pro Asp Trp Trp Ile Val Ser Ala Asp Tyr Ser Gln Ile Glu Leu
 1               5                  10                  15

Arg Ile Leu Ala His Leu Ser Gly Asp Glu Asn Leu Val Lys Ala Phe
            20                  25                  30

Glu Glu Gly Ile Asp Val His Thr Leu Thr Ala Ser Arg Ile Tyr Asn
        35                  40                  45

Val Lys Pro Glu Glu Val Asn Glu Met Arg Arg Val Gly Lys Met
    50                  55                  60

Val Asn Phe Ser Ile Ile Tyr Gly Val Thr Pro Tyr Gly Leu Ser Val
 65                  70                  75                  80

Arg Leu Gly Ile Pro Val Lys Glu Ala Glu Lys Met Ile Ile Ser Tyr
                85                  90                  95

Phe Thr Leu Tyr Pro Lys Val Arg Ser Tyr Ile Gln Gln Val Val Ala
            100                 105                 110

Glu Ala Lys Glu Lys Gly Tyr Val Arg Thr Leu Phe Gly Arg Lys Arg
        115                 120                 125

Asp Ile Pro Gln Leu Met Ala Arg Asp Lys Asn Thr Gln Ser Glu Gly
    130                 135                 140

Glu Arg Ile Ala Ile Asn Thr Pro Ile Gln Gly Thr Ala Ala Asp Ile
145                 150                 155                 160

Ile Lys Leu Ala Met Ile Asp Ile Asp Glu Glu Leu Arg Lys Arg Asn
                165                 170                 175

Met Lys Ser Arg Met Ile Ile Gln Val His Asp Glu Leu Val Phe Glu
            180                 185                 190

Val Pro Asp Glu Glu Lys Glu Glu Leu Val Asp Leu Val Lys Asn Lys
        195                 200                 205

Met Thr Asn Val Val Lys Leu Ser Val Pro Leu Glu Val Asp Ile Ser
    210                 215                 220

Ile Gly Lys Ser Trp Ser
    225             230
```

(2) INFORMATION FOR SEQ ID NO: 17:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

```
Gly Ser Arg Leu Val Asp Arg Gln Cys Gly Leu Phe Pro Asn Arg Thr
 1               5                  10                  15

Gln Asn Pro Arg Ser Ser Gln Trp
```

20

(2) INFORMATION FOR SEQ ID NO: 18:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

```
Glu Pro Cys Glu Gly Leu Arg Gly Gly His Arg Cys Ala His Leu Asp
 1               5                  10                  15

Cys Leu Gln Asp Leu Gln Arg Lys Ala Arg Arg Ser Glu Arg Arg Asn
                20                  25                  30

Ala Thr Gly Trp Lys Asp Gly Glu Leu Leu Tyr Asn Ile Arg Cys His
                35                  40                  45

Thr Val Arg Ser Phe Cys Glu Thr Trp Asn Thr Gly
                50                  55                  60
```

(2) INFORMATION FOR SEQ ID NO: 19:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

```
Arg Ser Arg Lys Asp Asp Tyr Gln Leu Phe His Thr Val Ser Lys Gly
 1               5                  10                  15

Ala Lys Leu His Pro Ala Gly Cys Cys Arg Gly Lys Arg Glu Gly Leu
                20                  25                  30

Arg Gln Asp Ser Leu Trp Lys Lys Lys Arg Tyr Ser Pro Ala His Gly
                35                  40                  45

Lys Gly Gln Glu His Pro Val Arg Arg Lys Asn Arg Asn Lys His
                50                  55                  60

Pro His Ser Gly Asn Cys Gly Arg Tyr Asn Lys Ile Gly Tyr Asp Arg
65                  70                  75                  80

Tyr Arg Arg Gly Ala Glu Lys Lys Lys His Glu Ile Gln Asn Asp His
                85                  90                  95

Ser Gly Ser
```

(2) INFORMATION FOR SEQ ID NO: 20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

```
Arg Thr Gly Leu Arg Gly Ser Arg
 1               5
```

(2) INFORMATION FOR SEQ ID NO: 21:

(i) SEQUENCE CHARACTERISTICS:

```
          (A) LENGTH: 6 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 21:

Gly Lys Arg Arg Thr Ser
     1               5

(2) INFORMATION FOR SEQ ID NO: 22:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 22:

Ser Gly Glu Glu Gln Asn Asp Lys Cys Gly Glu Thr Leu Cys Ala Ser
     1               5                   10                  15

(2) INFORMATION FOR SEQ ID NO: 23:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 23:

His Lys His Arg Lys Lys Leu Val Leu
     1               5

(2) INFORMATION FOR SEQ ID NO: 24:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 24:

Ile Gln Thr Gly Gly Ser Ser Val Arg Ile Ile Pro Lys
     1               5                   10

(2) INFORMATION FOR SEQ ID NO: 25:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 25:

Asn Ser Glu Ser Ser Leu Ile Ser Val Val Met Arg Thr Leu
     1               5                   10

(2) INFORMATION FOR SEQ ID NO: 26:

(i) SEQUENCE CHARACTERISTICS:
```

(A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

Arg Pro Ser Arg Arg Ala Ser Met Cys Thr Pro
    1               5                   10

(2) INFORMATION FOR SEQ ID NO: 27:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

Leu Pro Pro Gly Ser Thr Thr
    1               5

(2) INFORMATION FOR SEQ ID NO: 28:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 28:

Ser Gln Lys Lys
    1

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 29:

Thr Lys Lys Cys Asp Gly Leu Glu Arg Trp
    1               5                   10

(2) INFORMATION FOR SEQ ID NO: 30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 30:

Tyr Thr Val Ser His Arg Thr Val Phe Leu
    1               5                   10

(2) INFORMATION FOR SEQ ID NO: 31:

(i) SEQUENCE CHARACTERISTICS:

(A) LENGTH: 11 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 31:

Asp Leu Glu Tyr Arg Leu Lys Lys Gln Lys Arg
1               5                   10

(2) INFORMATION FOR SEQ ID NO: 32:

(i) SEQUENCE CHARACTERISTICS:
(A) LENGTH: 56 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 32:

Leu Ser Ala Ile Ser His Cys Ile Gln Arg Cys Glu Ala Thr Ser Ser
1               5                   10                  15

Arg Leu Leu Gln Arg Gln Lys Arg Arg Ala Thr Ser Gly Leu Ser Leu
            20                  25                  30

Glu Glu Lys Glu Ile Phe Pro Ser Ser Trp Gln Gly Thr Arg Thr Pro
        35                  40                  45

Ser Pro Lys Ala Lys Glu Ser Gln
        50                  55

(2) INFORMATION FOR SEQ ID NO: 33:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 33:

Thr Pro Pro Phe Arg Glu Leu Arg Gln Ile
1               5                   10

(2) INFORMATION FOR SEQ ID NO: 34:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 34:

Glu Lys Glu Thr
1

(2) INFORMATION FOR SEQ ID NO: 35:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: protein -continued

```
(xi) SEQUENCE DESCRIPTION: SEQ ID NO: 35:

Ser Phe Arg Phe Met Thr Asn Trp Ser Ser Arg Phe Pro Met Arg Lys
  1               5                   10                  15

Lys Lys Asn (2) INFORMATION FOR SEQ ID NO: 36:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 36:

Asn Ser Leu Cys Leu Leu Arg Leu Thr
  1               5

(2) INFORMATION FOR SEQ ID NO: 37:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 37:

Ala Ser Glu Lys Ala Gly Leu
  1               5
```